(12) United States Patent
Zahn et al.

(10) Patent No.: US 11,941,538 B2
(45) Date of Patent: Mar. 26, 2024

(54) SYSTEM AND METHOD FOR SAMPLE EVALUATION TO MIMIC TARGET PROPERTIES

(71) Applicant: Climax Foods Inc., Berkeley, CA (US)

(72) Inventors: Oliver Zahn, Berkeley, CA (US); Karthik Sekar, Berkeley, CA (US); Di Wei, Berkeley, CA (US); Sarah Hellmueller, Berkeley, CA (US); Daniel Westcott, Berkeley, CA (US); Sacha Laurin, Berkeley, CA (US)

(73) Assignee: Climax Foods Inc., Berkeley, CA (US)

( * ) Notice: Subject to any disclaimer, the term of this patent is extended or adjusted under 35 U.S.C. 154(b) by 0 days.

(21) Appl. No.: 18/220,110

(22) Filed: Jul. 10, 2023

(65) Prior Publication Data

US 2023/0376797 A1    Nov. 23, 2023

Related U.S. Application Data

(63) Continuation-in-part of application No. 18/202,174, filed on May 25, 2023, which is a continuation of application No. 18/098,898, filed on Jan. 19, 2023, now Pat. No. 11,823,070.

(60) Provisional application No. 63/301,948, filed on Jan. 21, 2022.

(51) Int. Cl.
*G06N 5/022* (2023.01)
(52) U.S. Cl.
CPC ................................. *G06N 5/022* (2013.01)

(58) Field of Classification Search
None
See application file for complete search history.

(56) References Cited

U.S. PATENT DOCUMENTS

| | | | |
|---|---|---|---|
| 10,957,424 | B1 | 3/2021 | Navon et al. |
| 11,205,101 | B1 | 12/2021 | Kawas Garcia et al. |
| 2017/0091637 | A1 | 3/2017 | Chae et al. |
| 2019/0171707 | A1 | 6/2019 | Rapaport |
| 2022/0005376 | A1 | 1/2022 | Pichara et al. |
| 2022/0104515 | A1 | 4/2022 | Hume et al. |
| 2023/0237345 | A1 | 7/2023 | Zahn et al. |

FOREIGN PATENT DOCUMENTS

CA    3083036 A1    11/2020

OTHER PUBLICATIONS

"Alternative Protein Company | Shiru", https://www.shiru.com/, first downloaded Oct. 20, 2022.
Day, Adrienne, "How one man's philosophy of data and food science could help save the planet", Grist.org, Nov. 10, 2020.
Shiebar, Jonathan, "Founded by an Impossible Foods and Google data scientist, Climax Foods raises $7.5 million to tackle the cheesiest market", Techcrunch, Sep. 1, 2020.
Watson, Elaine, "Climax Foods raises $7.5m: 'We want to replace animals as inefficient factories for converting plants into meat and dairy'", FoodNavigator-usa.com, Sep. 2, 2020.

*Primary Examiner* — Alan Chen
(74) *Attorney, Agent, or Firm* — Jeffrey Schox; Diana Lin

(57) ABSTRACT

In variants, a method for analog product determination can include: determining functional property feature values for a target and determining variable values for a prototype based on the functional property feature values for the target.

16 Claims, 23 Drawing Sheets sample

SYSTEM AND METHOD FOR SAMPLE EVALUATION TO MIMIC TARGET PROPERTIES

CROSS-REFERENCE TO RELATED APPLICATIONS

This application is a continuation-in-part of U.S. application Ser. No. 18/202,174 filed 25 May 2023, which is a continuation of U.S. application Ser. No. 18/098,898 filed 19 Jan. 2023, which claims the benefit of U.S. Provisional Application No. 63/301,948 filed 21 Jan. 2022, each of which is incorporated in its entirety by this reference.

TECHNICAL FIELD

This invention relates generally to the food science field, and more specifically to a new and useful system and method in the food science field.

DETAILED DESCRIPTION

The following description of the embodiments of the invention is not intended to limit the invention to these embodiments, but rather to enable any person skilled in the art to make and use this invention.

1. Overview

Figure 1:
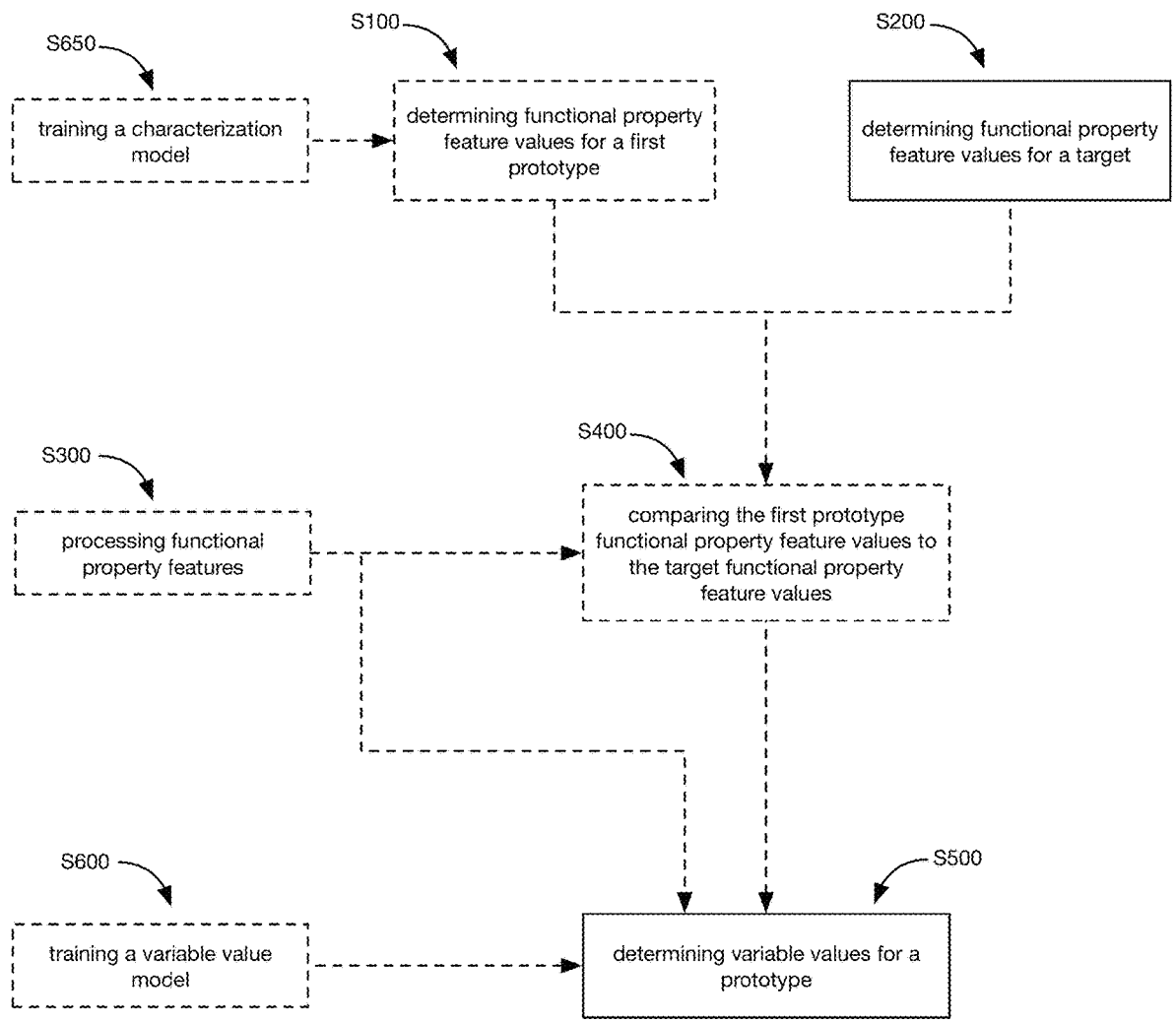
FIG. 1 is a schematic representation of a variant of the method.

As shown in FIG. 1, the method can include: determining functional property feature values for a target S200 and determining variable values for a prototype S500.

The method can function to determine the ingredients and/or process parameters that will substantially mimic the functional properties of a target (e.g., target food). In variants, the method can function to determine how similar a prototype is to a target, iteratively develop a prototype based on the proximity of the prototype's functional property feature values to a target (e.g., target functional property feature values), select features indicative of a given functional property (e.g., an objective or subjective measure), produce models capable of determining (e.g., predicting) a prototype's functional property feature values and/or otherwise characterizing a prototype, produce models capable of determining (e.g., predicting) how a prototype should be made (e.g., manufacturing variable values), and/or provide other functionalities.

2. Examples

In a first example, the method can include: measuring functional property signals for a prototype, extracting functional property feature values (e.g., signal feature values; non-semantic feature values) for the prototype from the prototype functional property signals; measuring functional property signals for a target, extracting functional property feature values for the target from the target functional property signals; and comparing the extracted prototype functional property feature values to the target functional property feature values (e.g., using a distance metric, using a clustering method, etc.). The comparison can be used to: select which prototype most closely mimics the target, determine how to adjust manufacturing variables for the next prototyping iteration, determine which manufacturing variables are most predictive of functional property differences, and/or be otherwise used.

In a second example, the method can include: using a trained model, predicting manufacturing variable values (e.g., ingredients, treatment specifications, etc.) that will produce a prototype with a target characterization (e.g., target functional property feature values, a target classification determined based on functional property feature values, etc.). The model can be trained using a set of characterized samples, wherein each sample is associated with variable values and a sample characterization value (e.g., functional property feature values extracted from a measured functional property signal, a classification determined based on functional property feature values, etc.). In an illustrative example, the method can determine a set of functional property feature values (e.g., signal features, non-semantic features, etc.) from measurements of each of a set of potential ingredients, that have optionally been treated using a set of process parameter values; and determining (e.g., predicting, inferring) which of the potential ingredients, process parameters, and/or quantities or values thereof would result in a similar analog to a target product, based on the functional property feature values. In a specific example, this can include predicting a combination of ingredients and/or process parameters that would have functional property feature values similar to a target's functional property feature values.

However, the method can be otherwise performed.

3. Technical Advantages

Variants of the technology can confer one or more advantages over conventional technologies.

First, evaluating substance analogs (e.g., food replicates) is difficult. The conventional method of sensory panels is impractical and inaccurate (because the results can be subjective), difficult to normalize, and noisy. Furthermore, sensory panels are practically inefficient to run, especially when testing a large number of food prototypes. Computational comparison of traditional material science features (e.g., food science features, functional property values) is also insufficient, because traditional (semantic) material science features are too coarse to adequately capture the nuances between different functional properties. For example, mouthfeel and texture can both be measured using rheology, but are experienced by a human in very different ways. The inventors have discovered that, surprisingly, comparing feature values (e.g., signal feature values, including values for non-semantic and/or semantic features) extracted from the raw functional property measurement signals—in addition to or in lieu of the conventional semantic features extracted from said signals—is a more accurate representation of the subjective (sensory) adjacency of a prototype to a target food.

Second, complex interactions between manufacturing variable values (e.g., specifying ingredients, manufacturing treatments, other sample specifications, etc.) can make predicting functional properties of a sample challenging. Variants of the technology can train a model to predict a set of manufacturing variable values that will produce a prototype with a target characterization (e.g., target functional property values, target classification, etc.). For example, variants of the technology can include training a model using feature values extracted from functional property signals, which can increase prediction accuracy and/or enable a smaller training dataset.

Third, variants of the technology can select a subset of functional property features which are predictive of a sample characterization, which can increase the accuracy and/or precision of the resultant prediction. For example, the subset of functional property features can be more representative of the subjective (sensory) characterization of the sample. In a first specific example, for each of a set of samples, functional property feature values are extracted from a measurement signal for the sample, wherein each sample is associated with a sample classification (e.g., dairy vs non-dairy). The functional property features can then be correlated with the sample classifications, and predictive functional property features can be selected for subsequent analysis based on the correlation. In a second specific example, lift analysis can be used (e.g., during and/or after training a characterization model) to select a subset of functional property features with high lift. This feature selection can reduce computational complexity and/or enable human-interpretable annotation of the features.

However, further advantages can be provided by the system and method disclosed herein.

4. System

The method can be used with one or more samples. The sample can be a product (e.g., food product) and/or be used to manufacture a product (e.g., an intermediate product). In examples, the sample can be a food product, material (e.g., leather, cloth, steel, etc.), gel, headspace, solution, mixture, component(s), ingredient(s), intermediate product, end-stage product, byproduct, and/or any other substance. The sample can be solid, liquid, gas, a combination thereof, and/or be any other state of matter.

In variants, samples can include prototypes, targets, and/or other substances.

A prototype is preferably a test sample that is intended to mimic a target (e.g., partially or in its entirety), but can alternatively be any other sample. For example, the prototype can be intended to have one or more characteristics (e.g., functional property signals, functional property values, functional property feature values, other characterization values, etc.) substantially similar to (e.g., within a predetermined margin of error, such as 1%, 5%, 10%, 20%, 30%, etc.) the target. For example, the prototype can be: a food analog or replicate (e.g., plant-based dairy analog), a material analog (e.g., plant-based leather), and/or any other substance. However, the prototype can be otherwise defined.

A target can function as an objective (e.g., gold standard, goal, etc.) for prototype evaluation. The target is preferably a target substance, but can additionally or alternatively be target functional property values, target functional property signals, target functional property feature values, other target characterization values (e.g., classifications, cluster locations, cluster identifiers, comparison metrics, etc.), a threshold thereof, a range thereof, and/or any other target. A target can be a positive target (e.g., where all or parts of the method can identify a prototype that is similar to the target) and/or negative target (e.g., where all or parts of the method can identify a prototype that is dissimilar to the target). However, the target can be otherwise defined.

In an example, a prototype can be: a replacement (e.g., analog) for a target food product (e.g., the prototype can be a plant-based analog for an animal food product), used to manufacture a target food product, a food product with one or more target characterization values, and/or any other food product. The prototype can be a vegan product, a food product without animal products and/or with less animal products (e.g., relative to a target animal product), a plant-based food product, a microbial-based food product, a nonmammalian-based food product, and/or any other food product. Examples of target food products include: dairy lipids (e.g., ghee, other bovine milk fats, etc.), milk, curds, cheese (e.g., hard cheese, soft cheese, semi-hard cheese, semi-soft cheese), butter, yogurt, cream cheese, dried milk powder, cream, whipped cream, ice cream, coffee cream, other dairy products, egg products (e.g., scrambled eggs), additive ingredients, mammalian meat products (e.g., ground meat, steaks, chops, bones, deli meats, sausages, etc.), fish meat products (e.g., fish steaks, filets, etc.), any animal product, and/or any other suitable food product. In specific examples, the target food product includes mozzarella, burrata, feta, brie, ricotta, camembert, chevre, cottage cheese, cheddar, parmigiano, pecorino, gruyere, edam, gouda, jarlsberg, and/or any other cheese. In a specific example, the prototype includes a milk analog (e.g., a functional milk analog for cow milk, sheep milk, goat milk, human milk, etc.).

The prototype is preferably entirely plant matter, but can additionally or alternatively be primarily plant matter (e.g., more than 50%, 60%, 70%, 80%, 90%, 95%, 98%, 99%, etc.), partially plant matter, and/or have any other suitable plant matter content. The prototype can optionally exclude and/or include less than a threshold amount of total and/or added: animal products (e.g., excludes animal proteins, such as caseins), gums (e.g., polysaccharide thickeners), allergenic ingredients (e.g., soy, peanut, wheat, etc.), and/or any other suitable ingredient. Added ingredients and/or compounds can include: materials that were not present in and/or are foreign to a plant substrate or other ingredients, materials added in as a separate ingredient, and/or otherwise other components. The threshold amount can be between 0.1%-50% or any range or value therebetween (e.g., 40%, 30%, 10%, 5%, 3%, 2%, 1%, 0.1%, etc.), but can alternatively be greater than 10% or less than 0.1%.

However, samples can be otherwise defined.

Each sample can optionally be associated with values (and/or ranges thereof) for: variables (e.g., to define the sample itself, the sample preparation process, etc.), functional properties, functional property features, other sample characterizations (e.g., classifications, clusters, etc.), and/or any other sample information. The values can be predetermined (e.g., predetermined variable values, a predetermined sample class such as 'dairy', etc.), predicted, measured, extracted from measurements, determined using a model, and/or otherwise determined. The system can optionally include a database, wherein sample information and/or associated values can be stored in the database or be otherwise stored.

Sample variable values (e.g., process parameters, manufacturing variable values, etc.) are preferably specifications prescribing the manufacturing of a sample, but can additionally or alternatively include a sample identifier and/or be otherwise defined. Variable values can define: manufacturing specifications; the amounts thereof (e.g., ratios, volume, concentration, mass, etc.); temporal parameters thereof (e.g., when the input should be applied, duration of input application, etc.); and/or any other suitable manufacturing parameter. Manufacturing specifications can include: ingredients, treatments, and/or any other sample manufacturing input, wherein each specification can be a variable and the variable values can include a value for each specification. Examples of treatments can include: adjusting temperature, adjusting salt level, adjusting pH level, diluting, pressurizing, depressurizing, humidifying, dehumidifying, agitating, resting, adding ingredients, removing components (e.g., filtering, draining, centrifugation, etc.), adjusting oxygen level, brining, comminuting, fermenting, mixing (e.g., homogenizing), gelling (e.g., curdling), and/or other treatments. Examples of variable values for treatments can include: treatment type, treatment duration, treatment rate (e.g., flow rate, agitation rate, cooling rate, rotor stator rpm, etc.), treatment temperature, time (e.g., when a treatment is applied, when the sample is characterized, etc.), and/or any other parameters.

Examples of ingredients can include: plant matter, proteins (e.g., protein isolates), a lipid component (e.g., fats, oils, etc.), an aqueous component (e.g., water, a sucrose solution, etc.), preservatives, acids and/or bases, macronutrients (e.g., protein, fat, starch, sugar, etc.), nutrients, micronutrients, carbohydrates (e.g., sugars, starches, fibers, polysaccharides, such as maltodextrin, gums, etc.), vitamins, enzymes (e.g., transglutaminase, chymosin, tyrosinase, bromelain, papain, ficain, other cysteine endopeptidases, rennet enzymes and/or rennet-type enzymes, etc.), emulsifiers (e.g., lecithin), particulates, hydrocolloids (e.g., thickening agents, gelling agents, emulsifying agents, stabilizers, etc, such as starch, gelatin, pectin, and gums, such as agar, alginic acid, sodium alginate, guar gum, locust bean gum, beta-glucan, xanthan gum, etc.), salts (e.g., NaCl, CaCl2, NaOH, KCl, NaI, MgCl2, etc.), minerals (e.g., calcium), chemical cross-linkers (e.g., transglutaminase) and/or non-crosslinkers (e.g., L-cysteine), coloring, flavoring compounds, vinegar (e.g., white vinegar), mold powders, microbial cultures, carbon sources (e.g., to supplement fermentation), calcium citrate, any combination thereof, and/or any other ingredient. The ingredients can optionally exclude and/or include less than a threshold amount (e.g., 10%, 5%, 3%, 3%, 1%, 0.5%, 0.1%, etc.) of added: animal products, animal-derived ingredients, gums (e.g., polysaccharide thickeners), hydrocolloids, allergens, phospholipids, and/or any other suitable ingredient. The ingredients are preferably food-safe, but can alternatively be not food-safe. The ingredients can be whole ingredients (e.g., include processed plant material), ingredients derived from plant-based sources, ingredients derived from plant genes, synthetic ingredients, and/or be any other ingredient.

Variable values (e.g., as an output of a variable value model) can optionally be constrained. Constraints can include binary constraints, thresholds, ranges, ratios, values, and/or any other constraints. In a first example, the constraints can include predetermined composition constraints of the resulting manufactured sample (e.g., a macronutrient constraint). In an illustrative example, the variable values are constrained to produce a sample with greater than a threshold concentration of protein. In a second example, constraints can be determined based on one or more metabolic models. For example, the constraint can ensure a microbe within the sample can perform a specified metabolic pathway (e.g., a binary constraint ensuring relevant reagents are present, a threshold constraint ensuring relevant reagents are present above a threshold concentration, etc.). In a third example, constraints can be learned (e.g., a learned constraint boundary). For example, the constraints can be learned during variable value model training, wherein the constraints ensure prototypes meet a target (e.g., a sample characterization target threshold, a binary sample characterization target, etc.). In an illustrative example, constraints are learned such that variable values that satisfy the constraints result in a shreddable prototype. However, the variable values can be otherwise constrained or unconstrainted.

However, sample variable values can be otherwise defined.

Functional properties can optionally function to characterize how the sample behaves during preparation and cooking (e.g., in the case of an intermediate sample used to create a food product) and/or to characterize the sample as an end-stage food product (e.g., in look, feel, taste, smell, etc.). Functional properties preferably represent behaviors at the macro-scale, but can additionally or alternatively represent behaviors at micro-scale, nano-scale, and/or any other scale. Functional properties (e.g., characteristics) can include: nutritional profile (e.g., macronutrient profile, micronutrient profile, etc.), nutritional quality (e.g., PD-CAAS score), amino acid score, protein digestibility (PD) score, texture (e.g., texture profile, firmness, toughness, puncture, stretch, compression response, mouthfeel, viscosity, graininess, relaxation, stickiness, chalkiness, flouriness, astringency, crumbliness, stickiness, stretchiness, tear resistance/strength, mouth melt, gooeyness, softness, etc.), solubility, melt profile, smoke profile, gelation point, flavor, appearance (e.g., color), aroma, precipitation, stability (e.g., room temperature stability), emulsion stability, ion binding capacity, heat capacity, solid fat content, chemical properties (e.g., pH, affinity, surface charge, isoelectric point, hydrophobicity/hydrophilicity, chain lengths, chemical composition, nitrogen levels, chirality, stereospecific position, etc.), physiochemical properties, compound concentration (e.g., in the solid sample fraction, vial headspace, olfactory bulb, post-gustation, etc.), denaturation point, denaturation behavior, aggregation point, aggregation behavior (e.g., micellization capability, micelle stability, etc.), particle size, structure (e.g., microstructure, macrostructure, fat crystalline structure, etc.), folding state, folding kinetics, interactions with other molecules (e.g., dextrinization, caramelization, coagulation, shortening, interactions between lipid and protein, interactions with water, aggregation, micellization, etc.), lipid leakage, water holding and/or binding capacity, lipid holding and/or binding capacity, fatty acid composition (e.g., percent saturated/unsaturated lipids), moisture level, turbidity, properties determined using an assay tool, and/or any other properties. However, functional properties can be otherwise defined.

A functional property signal is preferably a data series (e.g., data time series) associated with a functional property, but can additionally or alternatively be an array of values (e.g., an array of functional property values), an image, a video, and/or any other set of values. The functional property signal can be 1D, 2D, 3D, and/or any other number of dimensions. The functional property signal can optionally be a processed signal (e.g., an aggregate of signals, a smoothed signal, a transformed signal, a signal segment, a normalized signal, etc.). In a specific example, the processed signal can be an aggregate of signals across multiple samples, across multiple measurement trials (e.g., with the same or different samples), and/or any across other set. Functional property signals can be experimentally measured using an assay tool, determined based on other functional property signals, predicted, and/or otherwise determined. In specific examples, functional property signals can include measurements for: texture, melt, flavor, and/or any other functional property.

A functional property value is preferably a quantitative value associated with a functional property (e.g., viscosity, hardness, time to break, distance to failure, normalized work, diameter and/or area of melt spread, etc.), but can alternatively be a qualitative value (e.g., 'creamy') and/or otherwise defined. Functional property values can be objective (e.g., measured using an assay tool), subjective (e.g., determined using a human subject), and/or otherwise defined. Functional property values can be discrete, continuous, relative, a classification, numeric, binary, and/or be otherwise characterized. In a specific example, functional property values can be a binary characteristic (e.g., shreddable or non-shreddable). Functional property values can be calculated from the functional property signals, directly measured using an assay tool (e.g., without measuring a functional property signal), determined using one or more human subjects, predicted, and/or otherwise determined.

Functional property features can function to characterize measurement signals (e.g., functional property signals) and/or otherwise characterize the sample. The functional property features are preferably non-semantic features (e.g., non-human-interpretable; lacks a physical analog or physical interpretation), but can additionally or alternatively be semantic features. Functional property features can be parametric features, non-parametric features, and/or otherwise characterized. Functional property features can be features or characteristics of: a signal (e.g., a signal feature, the raw measurement signal itself, etc.), a time-series (e.g., spectral analyses, autocovariance, autocorrelation, statistical analyses, etc.), an image (e.g., edge, edgel, corner, blob, area, etc.), one or more measurements at a single time-point, functional property values (e.g., features extracted from functional property values, a functional property value itself, etc.), manufacturing information (e.g., features associated with the cost to manufacture the sample, carbon footprint and/or other sustainability measures of manufacturing, etc.), and/or be features or characteristics of any other sample information. However, functional property features can be otherwise defined.

Figure 2:
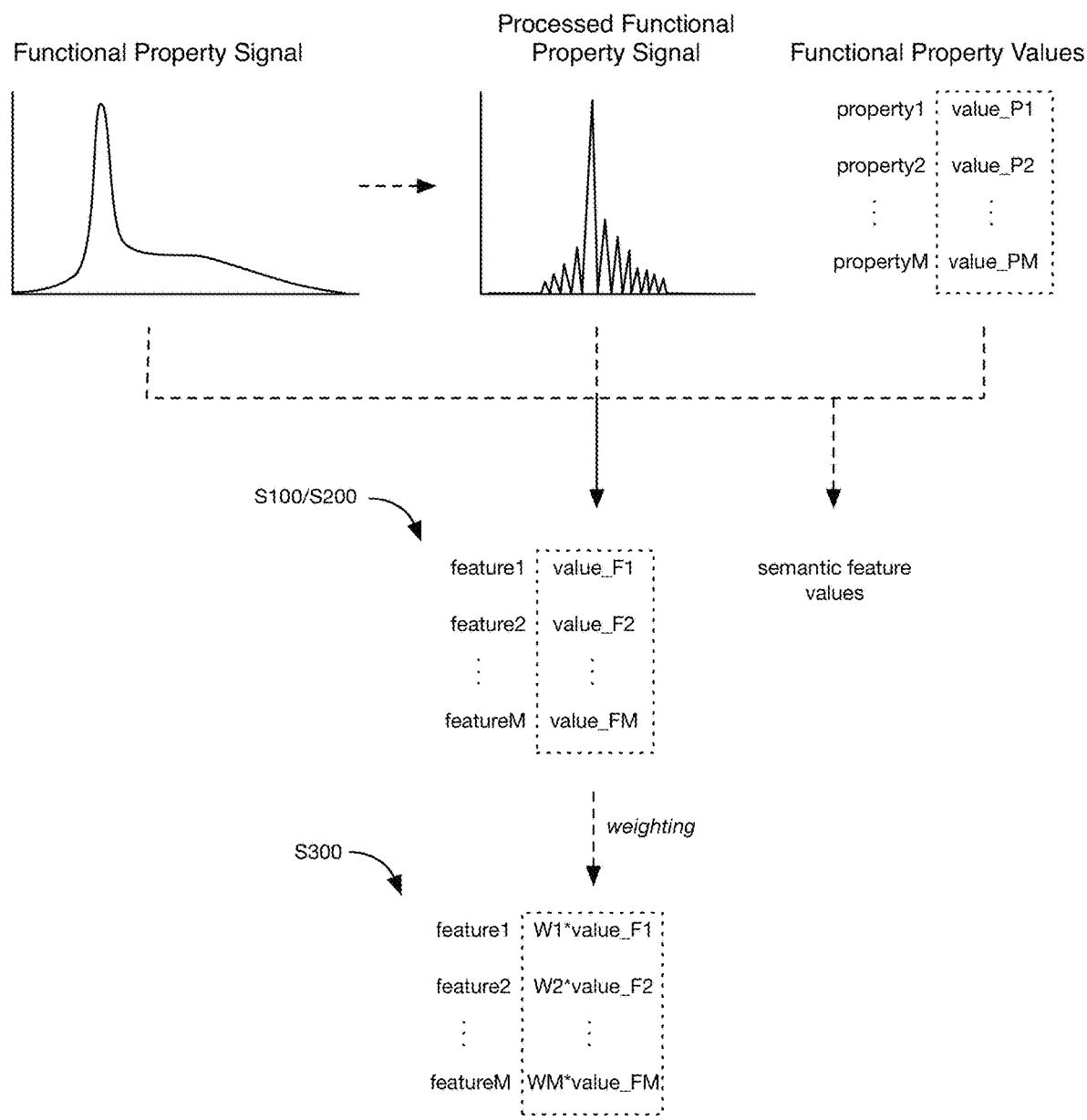
FIG. 2 depicts an example of determining functional property feature values.

Functional property feature values for a sample are preferably extracted from one or more functional property signals (e.g., directly calculated from the signal, based on signal analysis, etc.), but can additionally or alternatively be predicted (e.g., based on the sample variable values), directly determined using an assay, manually determined, randomly determined, and/or otherwise determined. In examples, functional property features values can be or include: values extracted from a functional property signal, values extracted from one or more measurements at a single time-point, the raw measurement signal, functional property values, values associated with the manufacturing (e.g., cost to manufacture the sample, carbon footprint and/or other sustainability measures of manufacturing, etc.), and/or be any other value associated with the sample. An example is shown in FIG. 2. In a specific example, functional property feature values are signal feature values that are extracted (e.g., using a feature extraction model) from time-series measurements taken during an experimental assay (e.g., rheology measurement) of a sample.

Variable values, functional property values, functional property signals, and/or functional property feature values can optionally include an uncertainty parameter (e.g., measurement uncertainty, determined using statistical analysis, etc.).

The system can optionally leverage one or more assays and/or assay tools to measure: functional property signals, functional property values, variable values, and/or any other sample information. Examples of assays and/or assay tools that can be used include: a differential scanning calorimeter (e.g., to determine properties related to melt, gelation point, denaturation point, etc.), Schreiber Test, an oven (e.g., for the Schreiber Test), a water bath, a texture analyzer (e.g., puncture test, compression test, extensibility assay, etc.), a rheometer, spectrophotometer (e.g., determine properties related to color), centrifuge (e.g., to determine properties related to water binding capacity), moisture analyzer (e.g., to determine properties related to water availability), light microscope (e.g., to determine properties related to microstructure), atomic force microscope (e.g., to determine properties related to microstructure), confocal microscope (e.g., to determine protein association with lipid/water), laser diffraction particle size analyzer (e.g., to determine properties related to emulsion stability), polyacrylamide gel electrophoresis system (e.g., to determine properties related to protein composition), mass spectrometry (MS), time-of-flight mass spectrometry (TOF-MS), gas chromatography (GC) (e.g., gas chromatography-olfactometry, GC-MS, etc.; to determine properties related to aroma/flavor, to determine properties related to protein composition, etc.), selected ion flow tube mass spectrometry (SIFT-MS), liquid chromatography (LC), LC-MS, fast protein LC (e.g., to determine properties related to protein composition), protein concentration assay systems, thermal gravimetric analysis system, thermal shift (e.g., to determine protein denaturation and/or aggregation behavior), ion chromatography, dynamic light scattering system (e.g., to determine properties related to particle size, to determine protein aggregation, etc.), Zetasizer (e.g., to determine properties related to surface charge), protein concentration assays (e.g., Q-bit, Bradford, Biuret, Lecco, etc.), particle size analyzer, sensory panels (e.g., human panelists to determine properties related to texture, flavor, appearance, aroma, etc.), capillary electrophoresis SDS (e.g., to determine protein concentration), spectroscopy (e.g., fluorescence spectroscopy, circular dichroism, etc.; to determine folding state, folding kinetics, denaturation temperature, etc.), absorbance spectroscopy (e.g., to determine protein hydrophobicity), CE-IEF (e.g., to determine protein isoelectric point/charge), total protein quantification, high temperature gelation, microbial cloning, Turbiscan, stereospecific analysis, olfactometers, electrophysiological testing (e.g., of a human olfactometer), psychophysical testing (e.g., of a human olfactometer), and/or any other assay and/or assay tool.

The system can include one or more models, including feature extraction models, feature selection models, characterization models, variable value models, correlation models, metabolic models, and/or any other model. The models can include or leverage: regression (e.g., leverage regression, etc.), classification, neural networks (e.g., CNN, DNN, CAN, LSTM, RNN, autoencoders, etc.), rules, heuristics, equations (e.g., weighted equations, etc.), selection (e.g., from a library), instance-based methods (e.g., nearest neighbor), regularization methods (e.g., ridge regression), decision trees, Bayesian methods (e.g., Naïve Bayes, Markov, etc.), Markov methods (e.g., hidden Markov models), kernel methods, deterministics, genetic programs, encoders, support vectors, association rules, ensemble methods, optimization methods, statistical methods (e.g., probability), comparison methods (e.g., matching, distance metrics, thresholds, etc.), dimensionality reduction (e.g., principal component analysis, t-distributed stochastic neighbor embedding, linear discriminant analysis, etc.), clustering methods (e.g., k-means clustering, hierarchical clustering, etc.), any machine learning model, and/or any other suitable method or model.

Models can be trained, learned, fit, predetermined, and/or can be otherwise determined. Models can be trained using self-supervised learning, semi-supervised learning, supervised learning, unsupervised learning, transfer learning, reinforcement learning, and/or any other suitable training method.

The feature extraction model can function to extract values for functional property features for a sample. The feature extraction model can output functional property feature values based on functional property signals (e.g., from one or more assays), functional property values, other measurements, variable values, and/or any other data. The feature extraction model can use: time series analysis, decomposition techniques (e.g., time series decomposition), sequence comparison techniques (e.g., dynamic time warping), subsequence discovery techniques, peak detection, signal transforms (e.g., Fourier transform, fast Fourier transform, Laplace transform, etc.), regression, image processing techniques, classifiers, Markov models, statistical methods, encoders (e.g., trained to encode functional property signals and/or variable values to a shared latent space), derivatives (e.g., first derivative, second derivative, third derivative, etc.), integrals (e.g., calculating an area under all or a portion of the functional property signal), and/or any other feature extraction methods.

The feature extraction model can optionally produce a processed functional property signal (e.g., a decomposed signal, a transformed signal, a signal segment, etc.), wherein the feature values are extracted based on the processed signal. An example is shown in FIG. 2.

Figure 12A:
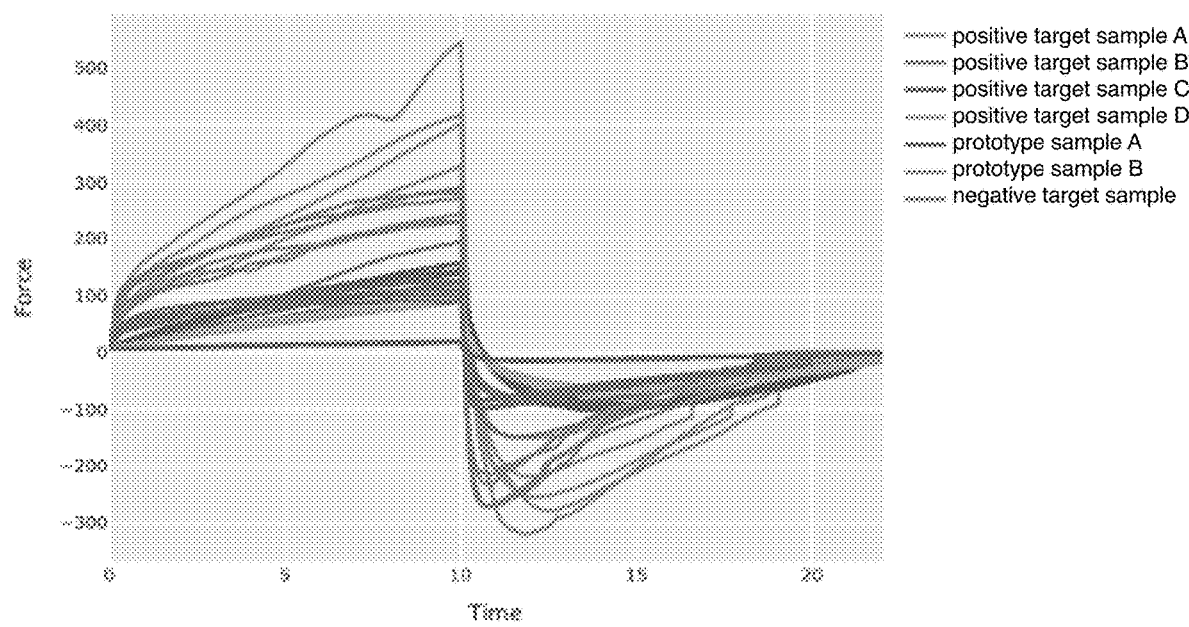
FIG. 12A depicts an illustrative example of functional property signals that were measured using a texture analyzer for positive target samples (e.g., dairy samples), negative target samples (e.g., non-dairy samples), and prototype samples.
Figure 12B:
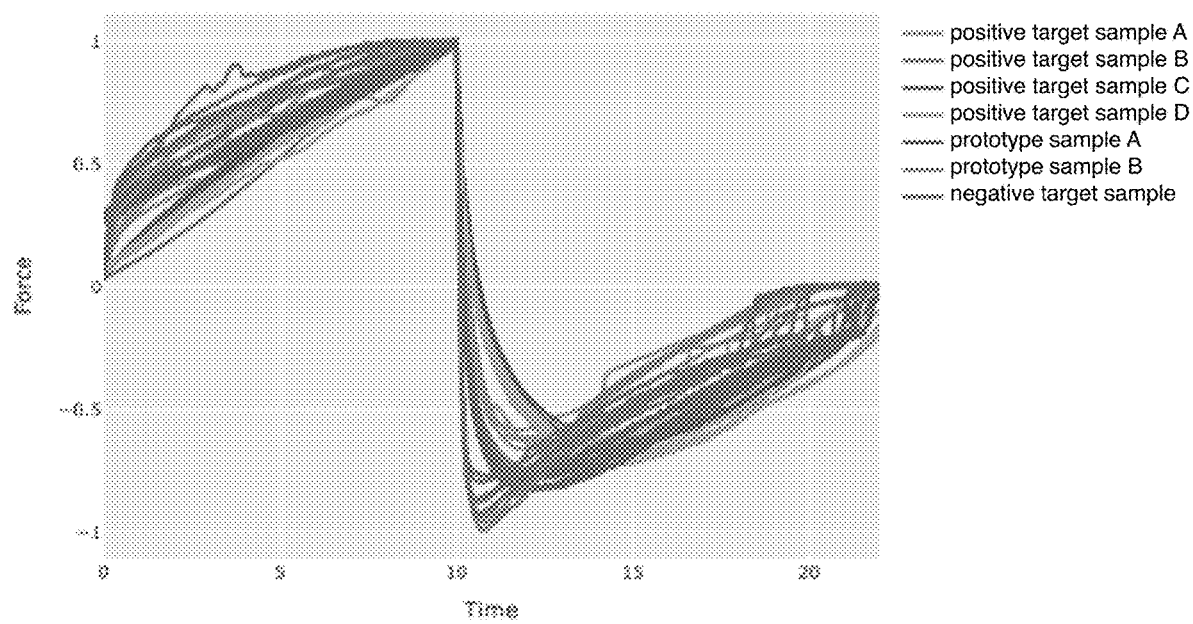
FIG. 12B depicts an illustrative example of normalized functional property signals for positive target samples (e.g., dairy samples), negative target samples (e.g., non-dairy samples), and prototype samples.
Figure 12C:
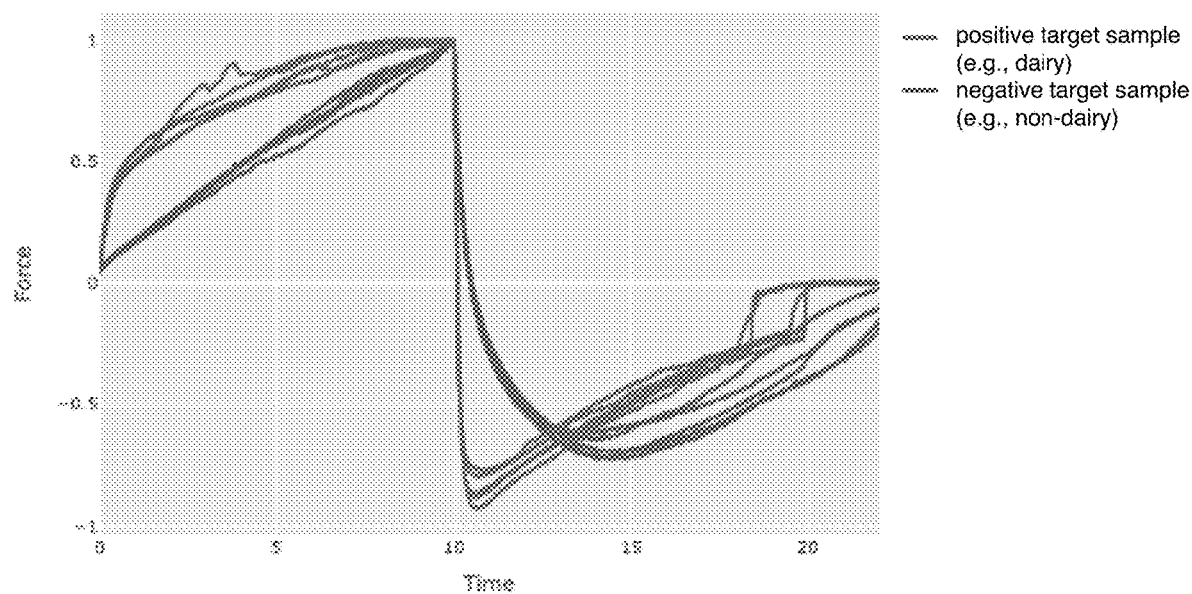
FIG. 12C depicts an illustrative example of normalized functional property signals for positive target samples (e.g., dairy samples) and negative target samples (e.g., non-dairy samples).

In a first example, the feature extraction model can produce a normalized signal from the functional property signal (e.g., from an unprocessed and/or processed functional property signal), wherein the prototype functional property feature values are extracted from the normalized prototype functional property signal. For example, the functional property signal can be normalized based on the peak of the functional property signal (e.g., normalized such that the peak is at a predetermined value such as 1; normalized such that the peak matches a peak of another functional property signal; etc.). Examples are shown in FIG. 12B and FIG. 12C. However, the functional property signal can be otherwise normalized.

Figure 11:
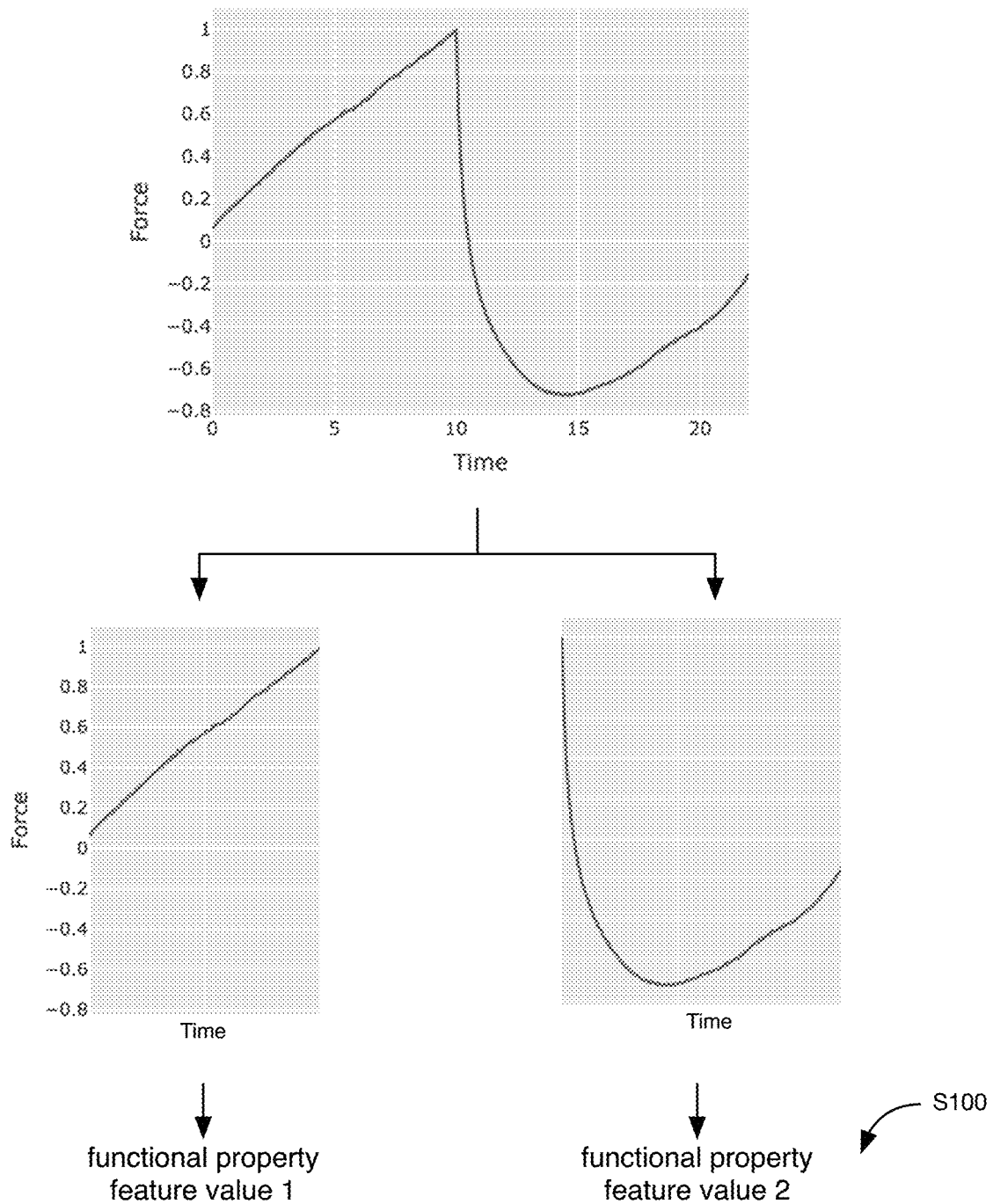
FIG. 11 depicts an illustrative example of determining functional property feature values using segments of the functional property signal.

In a second example, the feature extraction model can produce one or more segments (e.g., overlapping or non-overlapping portions) of the functional property signal (e.g., of an unprocessed and/or processed functional property signal), wherein the functional property feature values are extracted from the signal segments. An example is shown in FIG. 11. The number of signal segments can be 1, 2, 3, 4, 5, greater than 5, greater than 10, greater than 50, greater than 100, any range or value therebetween, and/or any other suitable number. In examples, the signal segments can be determined based on: time windows (e.g., a segment corresponds to a time window within the functional property signal), force thresholds (e.g., a segment includes a portion of the functional property signal with positive force values; a segment includes a portion of the functional property signal with negative force values; etc.), extension rate and/or strain rate thresholds (e.g., a segment includes a portion of the functional property signal with positive extension rate values; a segment includes a portion of the functional property signal with negative extension rate values; etc.), signal peaks (e.g., a segment includes data on either side of the signal peak; a segment includes data on one side of the signal peak; etc.), inflection points (e.g., when the force changes, when the extension rate changes, etc.), and/or any other suitable signal segmenting method. In a specific example, a first segment of a functional property signal is associated with a compressive force on a sample (e.g., the first segment corresponds to a portion of a texture analyzer test that includes puncturing the sample), and a second segment of the functional property signal is associated with tensile force on the prototype sample (e.g., the second segment corresponds to a portion of a texture analyzer test that includes pulling away from the sample after puncturing the sample). In an illustrative example, the first segment of the functional property signal includes a constant negative rate of extension (towards the sample), and the second segment of the functional property signal includes a constant positive rate of extension (away from the sample). The rate of extension (in the positive and/or negative direction) can be between 0.1 mm/s-100 mm/s or any range or value therebetween (e.g., 1 mm/s-10 mm/s, 2 mm/s, etc.), but can alternatively be less than 0.1 mm/s or greater than 10 cm/s. However, the functional property signal can be otherwise segmented.

In a third example, the feature extraction model can produce a transformed signal from the functional property signal (e.g., from an unprocessed and/or processed functional property signal), wherein the feature values are extracted based on the transformed signal. In examples, the transformed signal can include: a first derivative of the functional property signal (e.g., of the entire functional property signal, of a signal segment, etc.), a second derivative of the functional property signal, a third derivative of the functional property signal, an integration of the functional property signal (e.g., an area under the functional property signal), and/or any other signal transformation. In a specific example, the feature extraction model can produce at least one of: a first derivative of at least a portion of the functional property signal (e.g., of a first segment), a second derivative of at least a portion of the functional property signal (e.g., of a second segment), an integral of at least a portion of the functional property signal, and/or any other processed functional property signals. In an illustrative example, the feature extraction model can produce a first derivative of a compression functional property signal (e.g., a functional property signal and/or signal segment corresponding to negative extension rate), wherein sample softness can be determined based on the first derivative (e.g., a mean of the first derivative). In another illustrative example, the feature extraction model can produce a second derivative of a tensile functional property signal (e.g., a functional property signal and/or signal segment corresponding to positive extension rate), wherein sample gooeyness can be determined based on the second derivative (e.g., a maximum of the second derivative). However, the functional property signal can be otherwise transformed.

Figure 10:
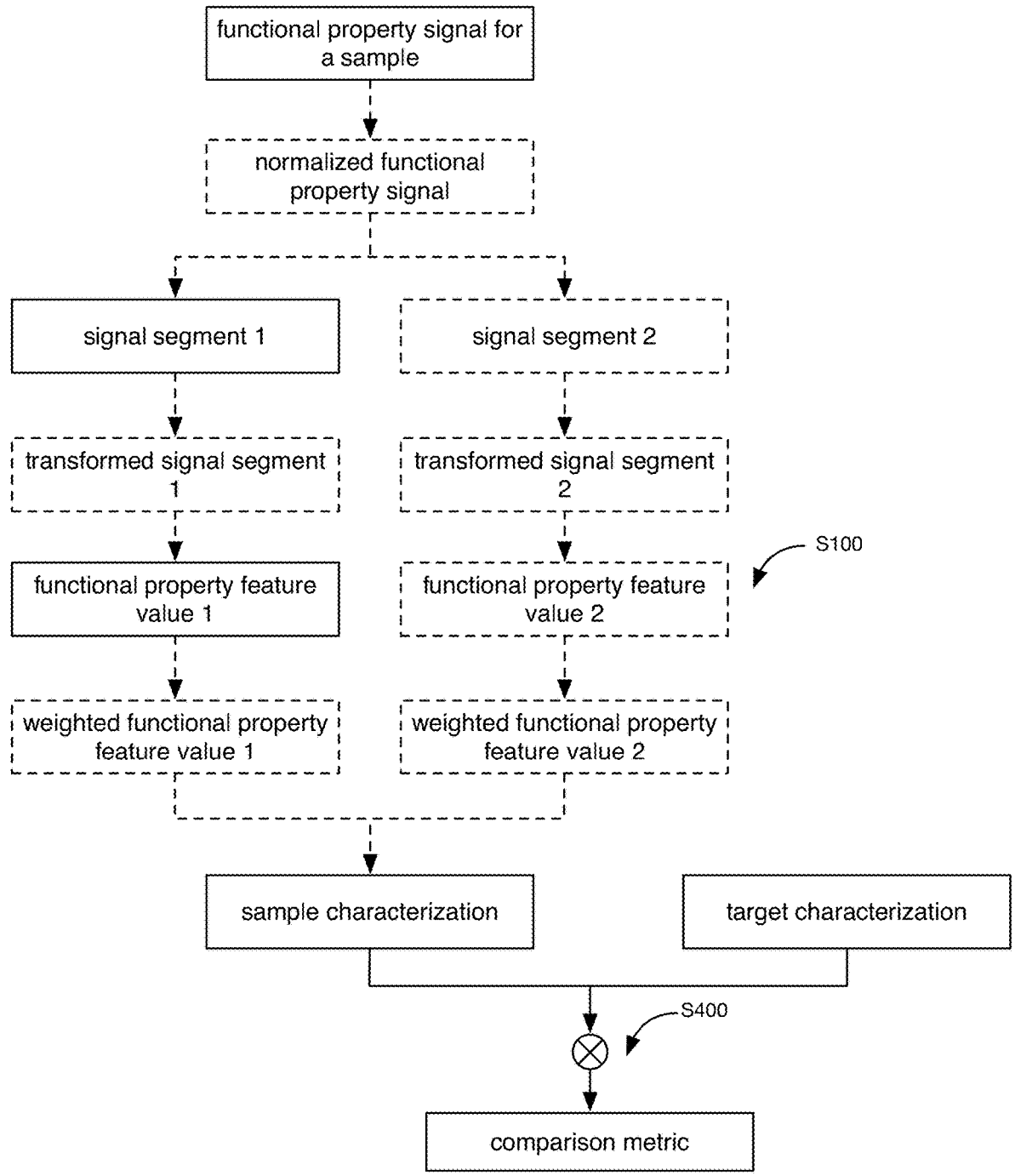
FIG. 10 depicts an example of the method, including determining functional property feature values using one or more segments of the functional property signal.

In a fourth example, the feature extraction model can produce a processed signal by (sequentially) processing the functional property signal using multiple methods. In an illustrative example, the functional property signal is normalized, segmented, and transformed (e.g., in any order) to produce one or more processed signal segments (e.g., a derivative of a segment of a normalized signal), wherein functional property feature values are extracted from the processed signal segments. An example is shown in FIG. 10.

However, the functional property signal can be otherwise processed.

The feature extraction model can be a single model, an ensemble model, and/or any other arrangement of one or more models. In a first example, the feature extraction model includes a first model that outputs non-semantic feature values based on one or more functional property signals and/or functional property values for a sample, and a second model that outputs semantic feature values based on one or more functional property values and/or functional property signals (e.g., the same functional property signals and/or different functional property signals). In a third example, the feature extraction model is a single model that outputs non-semantic feature values (e.g., only non-semantic feature values) based on one or more functional property signals, functional property values, and/or other data. In a fourth example, the feature extraction model is a single model that outputs a combination of semantic and non-semantic feature values based on one or more functional property signals, functional property values, and/or other data.

In a first embodiment, the feature extraction model can include and/or be based on predetermined model. In a first example, the feature extraction model can include a predetermined time series decomposition model, wherein the feature extraction model can extract feature values by decomposing a functional property signal into one or more components and determining the feature values based on the one or more components. In a second example, the feature extraction model can include a peak detection model, wherein a functional property feature value is based on a peak of the functional property signal (e.g., of an unprocessed or processed functional property signal). In a first illustrative example, the feature extraction model can extract distance to failure by determining a peak of a force versus extension signal. In a second illustrative example, the feature extraction model can extract firmness by determining a peak of a force versus time signal (from a texture analyzer). In a third example, the feature extraction model can include a statistical model, wherein the feature extraction model can extract a functional property feature value by determining a statistical measure (e.g., mean, maximum, minimum, etc.) of the functional property signal (e.g., of an unprocessed or processed functional property signal). In a specific example, functional property feature values can include: a statistical measure (e.g., maximum) of at least a portion of the functional property signal, a statistical measure (e.g., mean) of a first derivative of at least a portion of the functional property signal (e.g., of a first signal segment), a statistical measure (e.g., maximum) of a second derivative of at least a portion of the functional property signal (e.g., of a second signal segment), a statistical measure of an integral of at least a portion of the functional property signal, and/or any other functional property feature values. In an illustrative example, a value for sample softness can be determined based on a statistical measure (e.g., mean) of the first derivative of a compression functional property signal. In another illustrative example, a value for sample gooeyness can be determined based on a statistical measure (e.g., maximum) of the second derivative of a tensile functional property signal.

In a second embodiment, the feature extraction model can be trained on a predetermined training value for the feature (e.g., using supervised learning).

In a third embodiment, the feature extraction model can be a subset of the layers from a model trained end-to-end to predict another attribute (e.g., wherein the functional property features can be learned features). In a first illustrative example, the feature extraction model can be a subset of layers (e.g., the first several layers, feature extraction layers, intermediary layers, etc.) of a variable value model trained to predict variable values for a second prototype from: variable values, functional property signals, functional property values, and/or other inputs for a first prototype. In a second illustrative example, the feature extraction model can be a subset of layers of a characterization model trained to predict a sample characterization value from variable values, functional property signals, functional property values, and/or other inputs for the sample.

However, the feature extraction model can be otherwise configured.

The optional characterization model can function to determine (e.g., predict) one or more characterization values for a sample. A sample characterization value can include: a functional property signal; functional property value; functional property feature value; classification; cluster location; cluster identifier; comparison metric value between two samples (e.g., a prototype and a target); and/or any other parameter characterizing the sample. In variants, the characterization model can generate synthetic measurements and/or feature values for a hypothetical sample. In a first example, the sample characterization value is a vector, wherein each vector position can represent a different functional property feature and the vector value can represent the predicted value for said functional property feature. In a second example, the sample characterization value is a vector, wherein each vector position can represent a different functional property and the vector value can represent the predicted value for said functional property. In a third example, the sample characterization value is a classification. In a first illustrative example, the classifications include 'dairy' and 'non-dairy'. In a second illustrative example, the classifications include 'blue cheese', 'feta', 'plant-based blue cheese', and 'plant-based feta.' In a fourth example, the sample characterization value is a cluster identifier (e.g., 'blue cheese', 'dairy', 'plant-based cheese', etc.). In a fifth example, the sample characterization value is a cluster location (e.g., coordinates in feature space) representing: a point within a cluster, the cluster centroid, the cluster boundary, and/or any other location associated with one or more clusters. In a sixth example, the sample characterization is a comparison metric (e.g., as described in S400).

The characterization model inputs can include: variable values for a sample, functional property feature values for a sample, correlation information (e.g., outputs from the correlation model), and/or any other sample information. The characterization model outputs can include one or more sample characterization values and/or any other sample information. In a first variant, the characterization model outputs one or more sample characterization values based on functional property feature values associated with the sample (e.g., functional property feature values extracted from a measured functional property signal, functional property feature values predicted based on sample variable values using a different characterization model, etc.). In a second variant, the characterization model outputs one or more sample characterization values based on variable values associated with the sample. The characterization model can be trained via S650 and/or otherwise trained.

The characterization model can optionally interface with and/or be part of: a correlation model, feature selection model, and/or any other model (e.g., DNN, etc.). The characterization model can include a single model and/or multiple models. When the characterization model includes multiple models, the models can be arranged in series, in parallel, as distinct models, and/or otherwise arranged. When the characterization model includes multiple models, the models can be trained separately (e.g., using distinct training data sets), trained together (e.g., using the same training data set, using different subsets of the same training data set, etc.), and/or otherwise trained.

However, the characterization model can be otherwise configured.

The optional variable value model can function to determine (e.g., predict) variable values (e.g., for a second prototype) that would produce a prototype with a target characterization value and/or make a prototype more or less similar to a target.

The variable value model inputs can include: variable values for a sample (e.g., a first prototype), sample characterization values (e.g., comparison metric for the first prototype), a target (e.g., target sample characterization values), correlation information (e.g., outputs from the correlation model), and/or any other sample information. The variable value model outputs can include variable values for a sample (e.g., a second prototype), variable value adjustments (e.g., relative to variable values for a first prototype), and/or any other sample information. In a first variant, the variable value model outputs variable value adjustments for a second prototype based on sample characterization values (e.g., a comparison metric) for a first prototype. In a second variant, the variable value model outputs variable values for a prototype in a set of prototypes based on sample characterization values (e.g., the functional property feature values, the comparison metrics, etc.) for each of the set of prototypes. For example, a comparison metric can be determined for each of the set of prototypes (e.g., based on measured functional property signals, using a characterization model, using a first set of layers of the variable value model, etc.), wherein the top-ranked prototype and associated variable values (e.g., with the lowest comparison metric, highest comparison metric, etc.) is selected by the variable value model. In a third variant, the variable value model outputs variable values for a prototype based on a target characterization (e.g., associated with a target sample). For example, the target characterization can include target functional property values, target functional property feature values, a target classification, a target comparison metric, and/or any other target. In an illustrative example, the variable value model outputs variable values (e.g., binary include/exclude; amounts; etc.) for each of a set of candidate ingredients for the next prototype based on the functional property feature values for each ingredient and optionally the functional property feature values for the target. The variable value model can be trained via S600 and/or otherwise trained.

The variable value model can optionally interface with and/or be part of: a correlation model, feature selection model, characterization model, metabolic model (e.g., to ensure variable values satisfy one or more constraints), and/or any other model (e.g., DNN, etc.). The variable value model can include a single model and/or multiple models. When the variable value model includes multiple models, the models can be arranged in series, in parallel, as distinct models, and/or otherwise arranged. In an example, a characterization model and a variable value model can be used in series (e.g., wherein the characterization model determines a sample characterization for a first prototype and a variable model determines variable values for a second prototype based on the first prototype sample characterization). When the variable value model includes multiple models, the models can be trained separately (e.g., using distinct training data sets), trained together (e.g., using the same training data set, using different subsets of the same training data set, etc.), and/or otherwise trained.

However, the variable value model can be otherwise configured.

The optional correlation model can function to determine the correlation, interaction, and/or any other association between sample variables and sample characterizations (e.g., functional property features, classifications, clusters, etc.) and/or between functional property features and sample characterizations. The correlation model can use: classifiers, support vectors, artificial neural networks (ANNs), random fields (e.g., Markov random field, conditional random field, etc.), K-nearest neighbors, statistical methods, regression (e.g., coefficients, etc.), black box methods (e.g., LIME, SHAP values, contrastive explanations deconvolution, etc.), and/or any other method.

Figure 6:
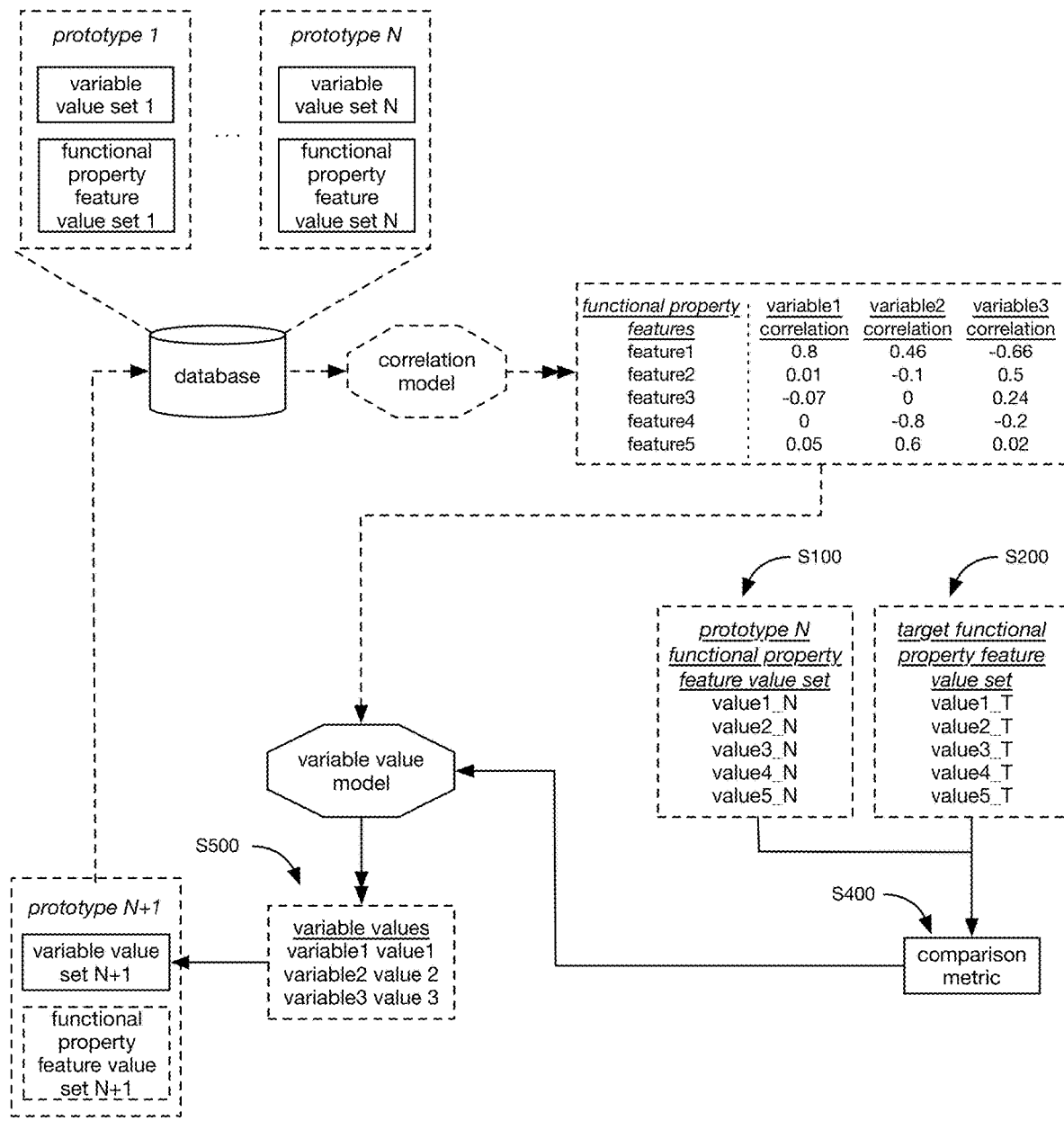
FIG. 6 depicts an illustrative example of determining variable values for a prototype.

In a first variant, the correlation model inputs can include variable values, sample characterization values (e.g., functional property values, classifications, cluster identifiers, cluster locations, comparison metrics, etc.; wherein the variable values and characterizations are associated via common samples), the system database, and/or any other information. The correlation model outputs can include a mapping between variables (e.g., variables, variable values, ranges of values, etc.) and sample characterizations (e.g., functional properties, functional property values, functional property features, functional property feature values, classifications, cluster identifiers, cluster locations, comparison metrics, ranges of values, etc.). The mapping can include: correlation coefficients (e.g., negative and/or positive), interaction effects (e.g., negative and/or positive, where a positive interaction effect can represent an increased significance effect of variable A on a sample characterization when in the presence of variable B), an association, confidence scores thereof, and/or other correlation metric. An example is shown in FIG. 6.

In a second variant, the correlation model inputs can include functional property feature values, sample characterization values (e.g., functional property values, classifications, cluster identifiers, cluster locations, comparison metrics, etc.; wherein the functional property feature values and characterizations are associated via common samples), the system database, and/or any other information. The correlation model outputs can include a mapping between functional property features (e.g., features, feature values, ranges of values, etc.) and sample characterizations (e.g., classifications, cluster identifiers, cluster locations, comparison metrics, ranges of values, etc.). The mapping can include: correlation coefficients, interaction effects (e.g., negative and/or positive, where a positive interaction effect can represent an increased significance effect of feature A on a sample characterization when in the presence of feature B), an association, confidence scores thereof, and/or other correlation metric.

The correlation model can optionally be trained on a set of characterized samples (e.g., characterized with: functional property signals, functional property feature values, functional property values, a classification, a cluster identifier, a cluster location, comparison metric, other characterization values, etc.). In a first variant, the correlation model can identify similar and/or divergent variable values (e.g., calculating an implicit and/or explicit similarity measure) between samples and correlate those variables to sample characterizations. For example, variables with differing values (e.g., across samples) can be mapped to the characterizations with differing values (e.g., across the same samples). In a second variant, the correlation model can identify similar and/or divergent functional property feature values between samples and correlate those functional property features to sample characterizations. For example, functional property features with differing values (e.g., across samples) can be mapped to the characterizations with differing values (e.g., across the same samples).

However, the correlation model can be otherwise configured.

The optional feature selection model can function to reduce feature dimensions, to select and/or weight features likely influencing (e.g., predictive of) sample characterizations, and/or to select and/or weight features representative of a human sensory evaluation. For example, the feature selection model can function to select a feature subset including features (e.g., predictors) that are relevant to: comparisons between a prototype and a target, one or more functional properties (e.g., hardness, creaminess, etc.), other sample characterizations, and/or other uses.

The feature selection model inputs can include: functional property features, functional property feature values, other sample characterizations (e.g., classifications, clusters, etc.), characterization values, correlation information (e.g., outputs from the correlation model, correlation coefficients, interaction effects, etc.), the system database, and/or any other sample information. The feature selection model outputs can include: a functional property feature subset, functional property feature weights (e.g., wherein features in the subset are weighted based on feature importance), and/or any other suitable outputs. The feature selection model can use: supervised selection (e.g., wrapper, filter, intrinsic, etc.), unsupervised selection, embedded methods, recursive feature selection, lift analysis (e.g., based on a feature's lift), any explainability and/or interpretability method (e.g., SHAP values), and/or any other selection method. The feature selection model can be a correlation model (and/or vice versa), can include a correlation model (and/or vice versa), can take correlation model outputs as inputs (and/or vice versa), be otherwise related to a correlation model, and/or be unrelated to a correlation model.

The feature selection model can optionally be trained to select relevant functional property features for sample characterization value determination and/or variable value determination. For example, the training target can be a subset of functional property features with high (positive and/or negative) interaction effects and/or correlation with sample characterizations (e.g., a correlation coefficient for a functional property feature given a target characterization value, interaction coefficients for functional property features, whether an expected correlation and/or interaction was validated and/or invalidated, etc.). However, the feature selection model can be otherwise trained.

However, the feature selection model can be otherwise configured.

The optional metabolic model can function to prescribe metabolic processes that can occur during the sample manufacturing process. The metabolic model can: specify variable values; dictate constraints for variable values (e.g., values for end-stage variables, ingredients that will result in target end-stage variables, etc.) and/or sample characterization values (e.g., predicted and/or otherwise determined); determine available metabolic pathways (e.g., based on sample variable values); and/or be otherwise used. Metabolic models can be implemented using domain knowledge of the metabolic pathways and/or be otherwise implemented. However, the metabolic model can be otherwise configured However, models can be otherwise defined.

All or part of the system and/or method can be implemented using a computing system. The computing system can include one or more: CPUs, GPUs, custom FPGA/ASICS, microprocessors, servers, cloud computing, and/or any other suitable components. The computing system can be local, remote (e.g., cloud), distributed, or otherwise arranged relative to any other system or module.

5. Method

As shown in FIG. 1, the method can include: determining functional property feature values for a target S200, and determining variable values for a prototype S500. The method can optionally include: determining functional property feature values for a first prototype S100, processing functional property features S300, comparing the first prototype functional property feature values to the target functional property feature values S400, training a variable value model S600, training a characterization model S650, and/or any other suitable steps.

All or portions of the method can be performed once (e.g., for a given target), multiple times (e.g., to develop a database of characterized samples), iteratively (e.g., to iteratively improve prototypes, to train a model, etc.), concurrently, asynchronously, periodically, in real time (e.g., responsive to a request), and/or at any other suitable time. All or portions of the method can be performed automatically, manually, semi-automatically, and/or otherwise performed. All or portions of the method can be performed by one or more components of the system, using a computing system, using a database (e.g., a system database, a third-party database, etc.), by a user, and/or by any other suitable system. The method is preferably performed for a combination of functional properties of a target for each iteration (e.g., the resultant sample has values for functional properties similar to values for multiple functional properties of the target), but can alternatively be performed for a single functional property (e.g., the sample has value(s) for a single functional property similar to the target value(s) for the functional property; the sample is iteratively refined on a functional property-by-functional property basis) and/or for any other suitable number of functional properties for each iteration.

The method can optionally include determining functional property feature values for a first prototype S100, which functions to characterize functional property signals measured for the first prototype. S100 can be performed after a physical prototype has undergone one or more experimental assays (e.g., after functional property measurement signals have been determined), without performing experimental assays, and/or at any other time. S100 can be performed after the prototype has been manufactured, during manufacturing, without manufacturing a physical prototype (e.g., in the case of predicted functional property feature values), and/or at any other time. S100 can be performed one or more times for each prototype, wherein multiple values for a given functional property feature can optionally be aggregated (e.g., averaged, summed, etc.). S100 can optionally be repeated for each prototype in a set of prototypes.

The first prototype's functional property feature values can be extracted, predicted (e.g., based on the first prototype variable values, using a characterization model), predetermined, determined manually, determined automatically, determined with a model (e.g., a feature extraction model), retrieved from a database (e.g., where prototype functional property feature values are those associated with the prototype in a database), synthetically generated, determined randomly, and/or be otherwise determined.

Figure 7:
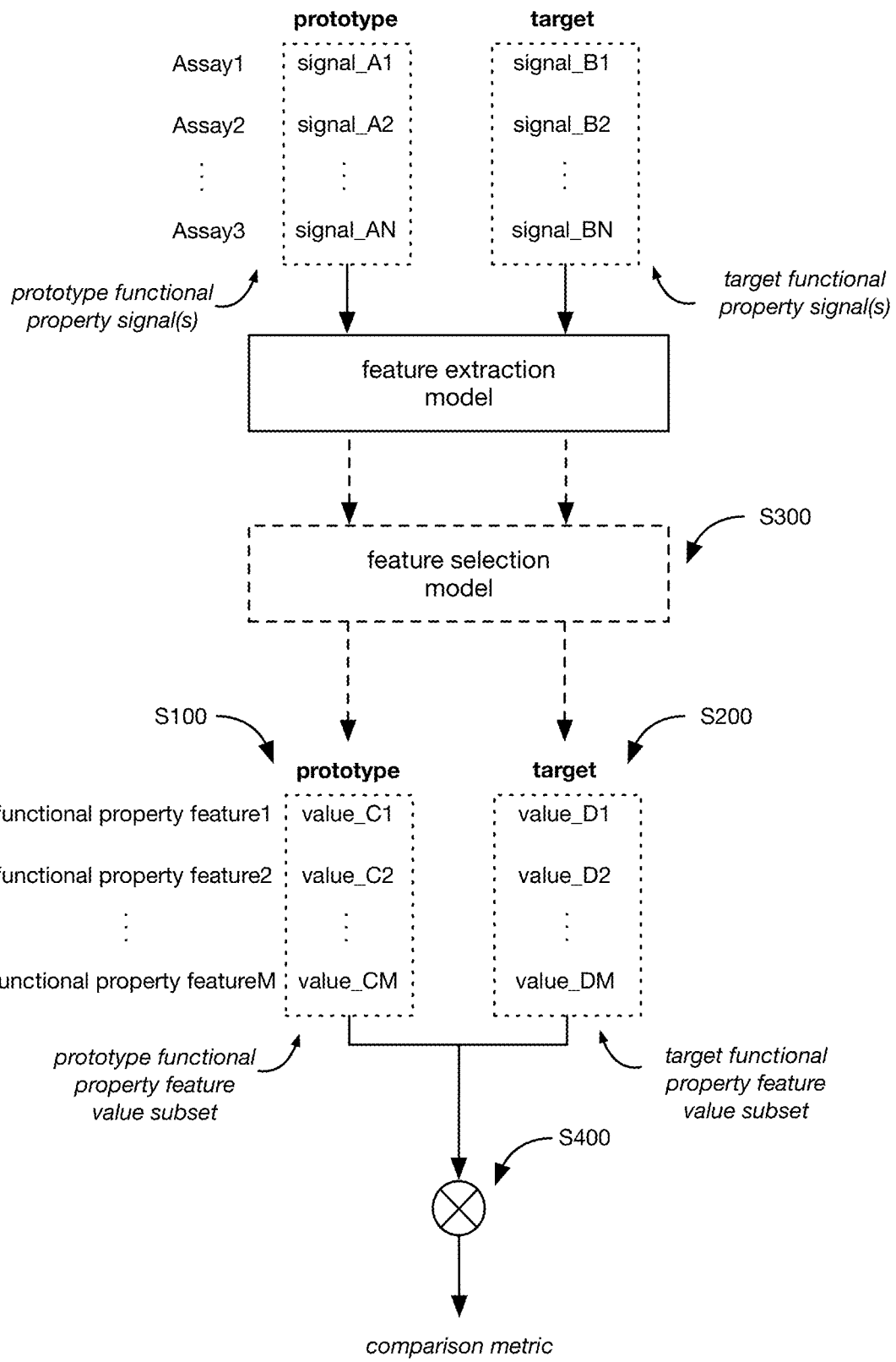
FIG. 7 depicts an example of extracting prototype functional property feature values and target functional property feature values.

In a first variant, S100 can include measuring one or more functional property signals using an assay and/or assay tool, optionally extracting signal feature values (e.g., where the functional property feature values includes the signal feature values) from the functional property signals (e.g., using a feature extraction model), and/or optionally extracting functional property values from the functional property signals (e.g., where the functional property feature values includes the functional property values). S100 can optionally include aggregating multiple functional property signals (e.g., texture signal, rheology signal, etc.), and extracting signal features from the aggregated signals. S100 can optionally include aggregating functional property feature values (e.g., into a single set of functional property values), wherein the functional property feature values can be determined using different measurement modalities (e.g., different assays); an example is shown in FIG. 7. In all or parts of the method, the measurement protocol (e.g., assay protocol) for different samples (e.g., samples that are compared against each other such as prototypes and targets) are preferably the same, but can alternatively be different.

Figure 14:
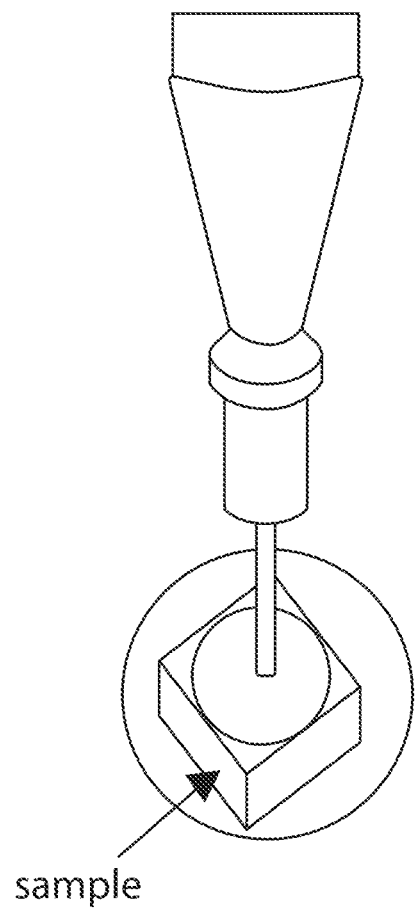
FIG. 14 depicts an example image of measuring a functional property signal for a sample using a texture analyzer.

In a first example, a texture signal (e.g., including force and/or extension/displacement versus time, including force versus extension/displacement, etc.) for a food prototype can be measured using a texture analyzer. An example of texture signals is shown in FIG. 12A. The texture signal can be from: a puncture test, a texture profile analysis (e.g., a compression test), an extensibility assay, and/or any other texture test or measurement. An example is shown in FIG. 14. The feature extraction model can extract a set of signal feature values from the texture signal (e.g., time series characteristics extracted using time series analysis techniques). In an illustrative example, this can include: subjecting the prototype to a puncture test, sampling the puncture test waveforms, and extracting signal features from each puncture test waveform. The texture signal can additionally or alternatively be used to determine functional property values (e.g., values for hardness, spreadability, distance to failure, normalized work, etc.).

In a second example, S100 can include: measuring the rheology of a prototype, obtaining the rheology measurement signal (e.g., raw signal), and extracting signal features from the measurement signal.

In a third example, S100 can include: subjecting the prototype to a Schreiber test, sampling a time series of images throughout the test, and extracting image features from at least a subset of the images (e.g., prototype area, radius, distribution of edges, histogram of gradients, etc.).

In a fourth example, S100 can include: using a GC-MS assay tool to measure odorants and/or any molecules in the volatile phase for a sample (e.g., from a gaseous headspace, from human breath after tasting a sample, etc.), and directly determining flavor functional property feature values from the measurement values (e.g., where the feature values are the measurement values, where the feature values are processed measurement values, etc.).

In a fifth example, S100 can include: determining a first set of nutritional quality functional property feature values (e.g., via a PDCAAS method, retrieving the values from a database, etc.), and optionally extracting a second set of nutritional quality functional property feature values from amino acid sequences of proteins in the sample.

In a sixth example, S100 can include using one or more human panelists to evaluate a functional property (e.g., a binary evaluation, a subjective score, etc.), and determining functional property feature values based on the panelist evaluation(s). For example, the functional property feature values can be the panelist evaluation(s), be an aggregate of evaluations, be extracted from the evaluation(s), and/or be otherwise determined based on the evaluations.

In a second variant, S100 can include predicting functional property feature values based on variable values for the first prototype using the characterization model (e.g., trained via S650).

However, prototype functional property feature values can be otherwise determined.

Determining functional property feature values for a target S200 functions to specify one or more criteria for prototype evaluation. S200 can be performed after a physical target has undergone one or more experimental assays (e.g., the same experimental assays as S100), without performing experimental assays, and/or at any other time. S200 can be performed after the target has been manufactured, during manufacturing, without manufacturing a physical target (e.g., in the case of predetermined target characterization values), and/or at any other time. S200 can be performed one or more times for a target, wherein multiple values for a given functional property feature can optionally be aggregated (e.g., averaged, summed, etc.).

The target's functional property feature values can be extracted, predicted (e.g., based on the target variable values, using a characterization model), predetermined, determined manually, determined automatically, determined with a model (e.g., a feature extraction model), retrieved from a database (e.g., where target functional property feature values are those associated with the target in a database), synthetically generated, determined randomly, and/or be otherwise determined.

S200 can be performed using any methods described in S100. S200 is preferably performed in a similar manner to S100 (e.g., leverages the same methodologies, using the target instead of the prototype, etc.), but can alternatively be different. The assay types, assay protocols, transformations, feature extraction methods, and extracted functional property features are preferably the same for S200 as in S100, but can additionally or alternatively be different.

However, target functional property feature values can be otherwise determined.

The method can optionally include processing functional property features S300, which functions to select and/or weight features likely influencing (e.g., having a measurable effect on, a significant effect on, a disproportionate effect, etc.) sample characterizations, to select and/or weight features representative of a human sensory evaluation, and/or to reduce feature space dimensions (e.g., to reduce computational load). S300 can be performed after S100, after S200, after S400, before S400, before S500, during S600, after S600, during S650, after S650, and/or at any other time.

Processing functional property features can include weighting the features, selecting a subset of the features, aggregating features, and/or otherwise processing the features. The features can be processed using a feature selection model, using a correlation model, randomly, with human input, and/or be otherwise processed. In all or parts of the method, functional property features can optionally be processed functional property features (e.g., a subset of functional property features, weighted functional property features, aggregated functional property features, etc. etc.), wherein functional property feature values are values for the processed functional property features.

In a first variant, the functional property features can be processed (e.g., selected and/or weighted) based on the influence of each functional property feature on sample characterization. In a first embodiment, the feature selection model uses lift analysis (e.g., applied to a trained characterization model and/or a trained variable value model) to weight features based on their associated lift and/or to select the subset of features with lift above a threshold. In a second embodiment, functional property features are processed based on their associated weights used for the characterization model and/or variable value, wherein the model weights can be determined during and/or after model training. For example, functional property features with model weights above a threshold value are selected as a functional property feature subset. In a third embodiment, a correlation model can be used to determine functional property features positively and/or negatively correlated to one or more sample characterizations (e.g., absolute value of correlation coefficient above a threshold, a confidence score above a threshold, etc.).

In a second variant, a subset of functional property features can be determined using any dimensionality reduction technique (e.g., principal component analysis, linear discriminant analysis, etc.).

In a third variant, functional property features can be processed (e.g., selected and/or weighted) based on a comparison between a target and a prototype (e.g., via S400 methods), wherein the functional property features can be processed based on the comparison (e.g., wherein the processed functional property features can be used for analysis of a second prototype). For example, a difference between functional property feature values associated with the target and prototype can be determined (e.g., where one or more sample characterization values differ between the two sets). The functional property features associated with the differing functional property feature values can define the functional property feature subset and/or be given higher weights.

In a fourth variant, functional property features can be processed using predetermined weights for each functional property feature. For example, a sample characterization can be determined by weighting each functional property feature value according to a corresponding functional property feature weight. In examples, the sample characterization can be aggregated weighted functional property feature values, a location of the weighted functional property feature values in feature space, and/or any other sample characterization. In a specific example, a characterization can include a weighted aggregation of at least a first prototype functional property feature value and a second prototype functional property feature value.

However, the functional property features can be otherwise processed.

The method can optionally include comparing the first prototype functional property feature values to the target functional property feature values S400, which functions to determine whether the first prototype has a desired characterization (e.g., whether the prototype is similar to or dissimilar from the target). The target functional property feature values can be determined using another iteration of S100-S300 (e.g., using the target instead of the prototype or sample), but can be otherwise determined. S400 can be performed after S100, after S200, after S300, and/or any other time. S400 can be performed for each measurement assay, performed for multiple subsets of the functional property feature values (e.g., performed once for flavor feature values, once for texture feature values, etc.), performed for all functional property feature values (e.g., aggregated across feature values extracted from measurements acquired via differing assay tools), and/or be otherwise performed.

Comparing prototype functional property feature values to the target functional property feature values preferably includes determining a comparison metric (e.g., to quantify, classify, and/or otherwise define similarity). The comparison metric can be qualitative, quantitative, relative, discrete, continuous, a classification, numeric, binary, and/or be otherwise characterized. The comparison metric can be or include: a distance (e.g., Euclidean distance), difference, ratio, regression, residuals, clustering metric (e.g., wherein multiple samples of the first prototype and/or targets are evaluated, wherein multiple prototypes and/or targets are evaluated, etc.), statistical measure, rank, classification, vector, functional property features and/or values thereof, any similarity metric, and/or any other comparison measure. In an example, the comparison metric is a distance in functional property feature space (e.g., wherein a functional property value set for a sample is an embedding in the feature space). In a specific example, the comparison metric is a distance between a prototype characterization (e.g., a location of a set of prototype functional property feature values in feature space) and a target characterization (e.g., a location of a set of target functional property feature values in feature space). In an illustrative example, the comparison metric is low (e.g., the first prototype is similar to the target) when the first prototype functional property feature values are near (in feature space) positive target functional property feature values and/or far from negative target functional property feature values. The comparison metric can optionally include metrics for variance and/or any other statistical measure (e.g., for a single prototype, for multiple prototypes with similar variable values, for a cluster of functional property feature values, etc.).

The comparison metric can be determined using the characterization model, comparison methods (e.g., matching, distance metrics, etc.), thresholds, regression, selection methods, classification, neural networks (e.g., CNNs, DNNs, etc.), clustering methods, rules, heuristics, equations (e.g., weighted equations, etc.), and/or any other methods.

In a first variant, the comparison metric can be determined using clustering analysis. Functional property feature values (e.g., for the first prototype, for the target, for other samples, etc.) can be clustered, wherein the comparison metric is determined based on the clusters. The clustering dimensions can be based on individual features, aggregate features, weighted features, otherwise processed features, learned dimensions, and/or any other dimensions in feature space. Cluster analyses can include connectivity-based clustering (e.g., hierarchical clustering), centroid-based clustering, distribution-based clustering, density-based clustering, grid-based clustering, and/or any other cluster analysis.

Figure 13A:
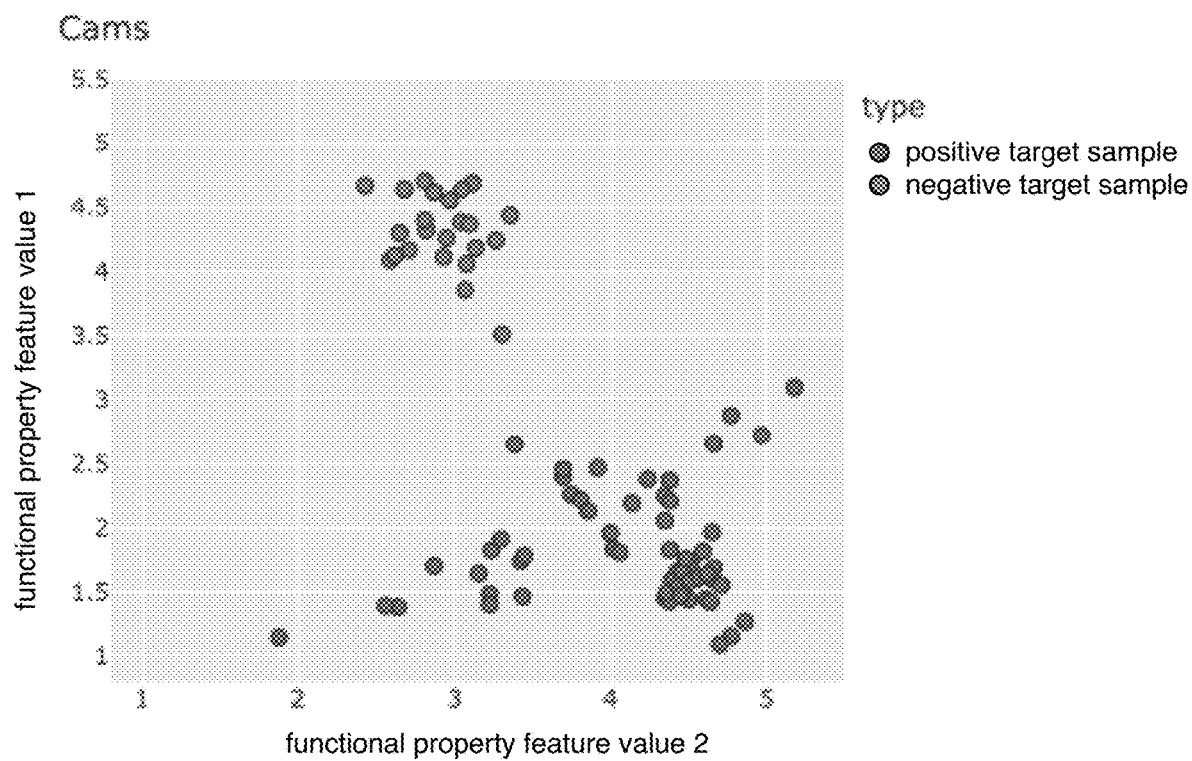
FIG. 13A depicts an illustrative example of clustered positive target samples (e.g., dairy samples) and clustered negative target samples (e.g., non-dairy samples).
Figure 13B:
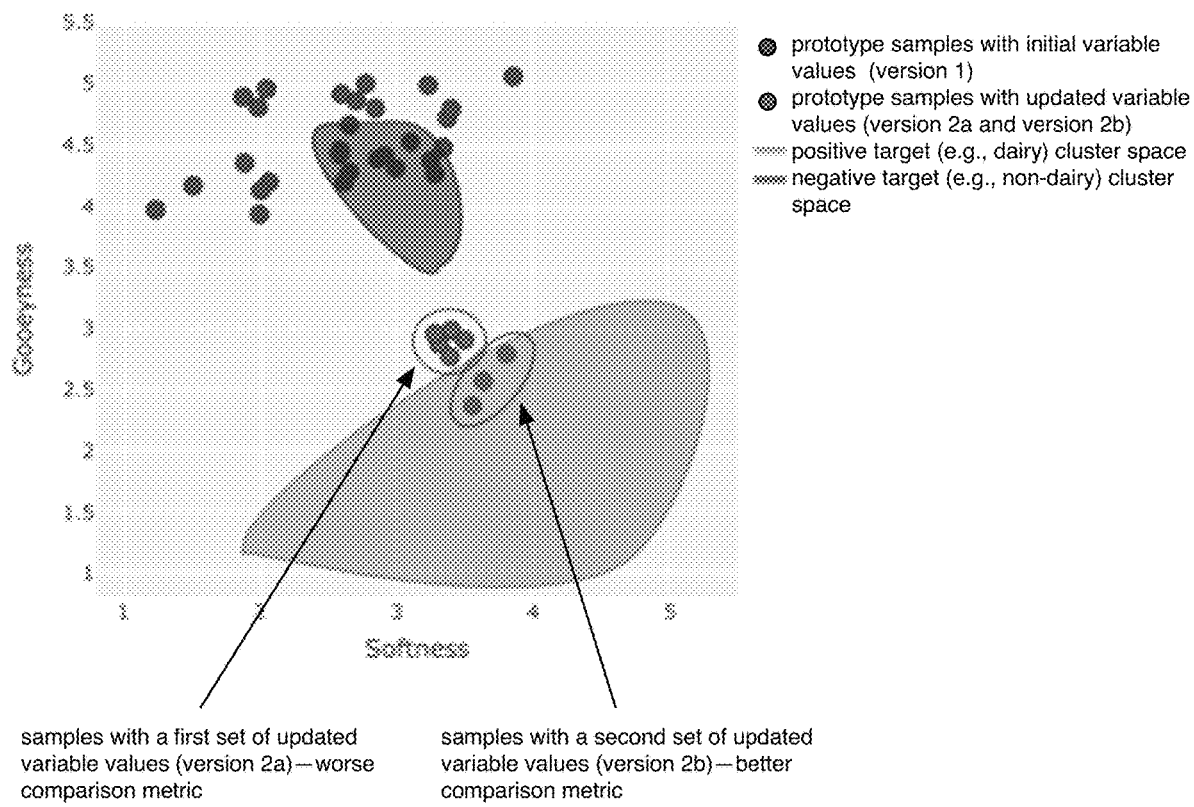
FIG. 13B depicts an illustrative example of prototype samples compared to target cluster spaces (e.g., a positive target cluster space and a negative target cluster space determined based on the positive target cluster and the negative target cluster, respectively, from FIG. 13A).

In a first embodiment, clustering is supervised (e.g., the characterization model is trained using labeled functional property value sets). Examples are shown in FIG. 13A and FIG. 13B. In a first example, sets of functional property feature values for sample instances (e.g., prototype instances, target instances) with the same variable values are clustered together (e.g., labeled with the same, known cluster identifier). In a second example, sets of functional property feature values for sample instances with the same sample class (e.g., a predetermined sample class) are clustered together. In a first illustrative example, multiple varieties of blue cheeses can be clustered together (e.g., where the target is the blue cheese class). In a second illustrative example, multiple instances of the same specific blue cheese type (within a larger blue cheese class) can be clustered together (e.g., where the target is the specific blue cheese type). In a second embodiment, clustering is unsupervised. For example, the characterization model can be trained using sets of characterized samples, each with a functional property value set, wherein clusters of samples are learned.

Figure 8:
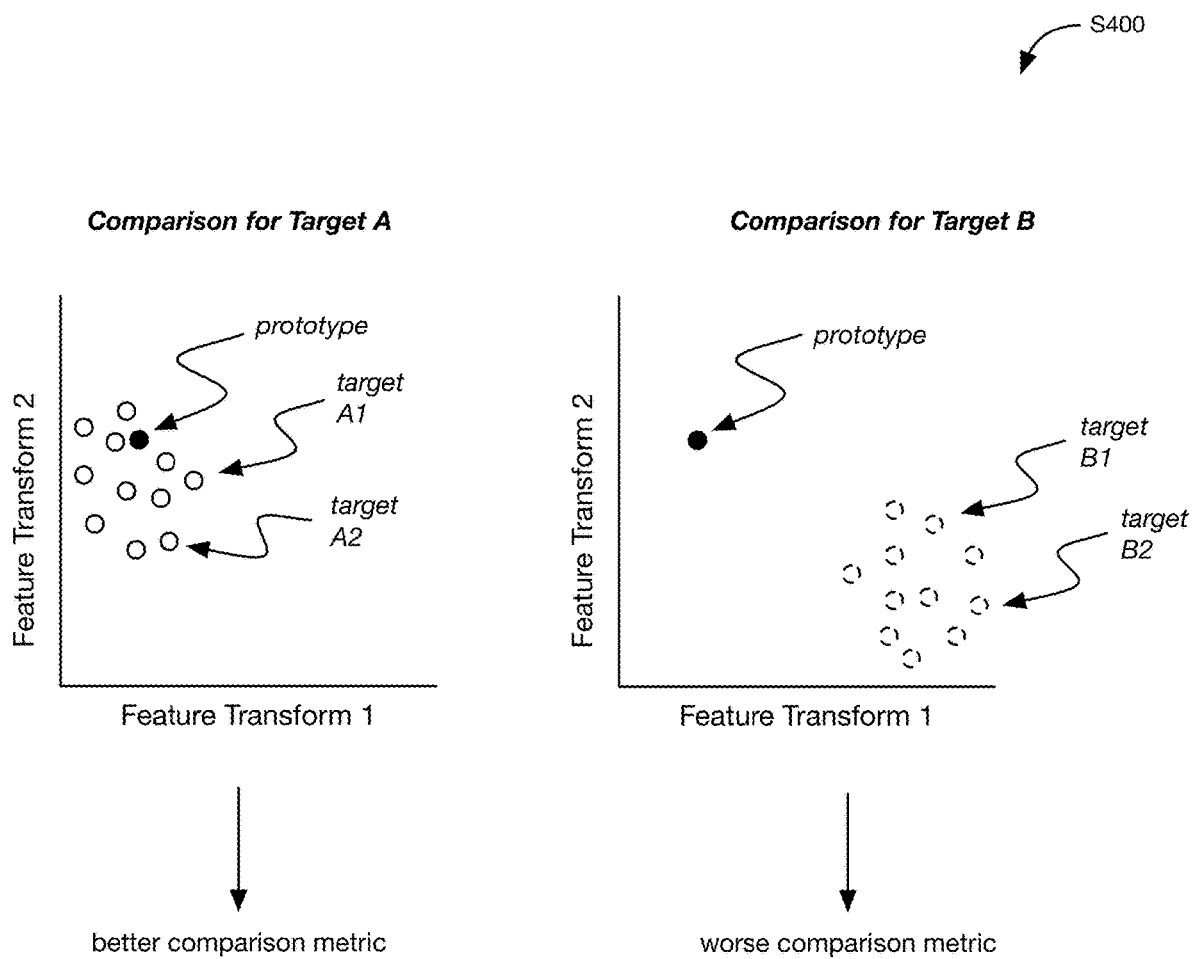
FIG. 8 depicts a first illustrative example of a comparison metric.
Figure 9A:
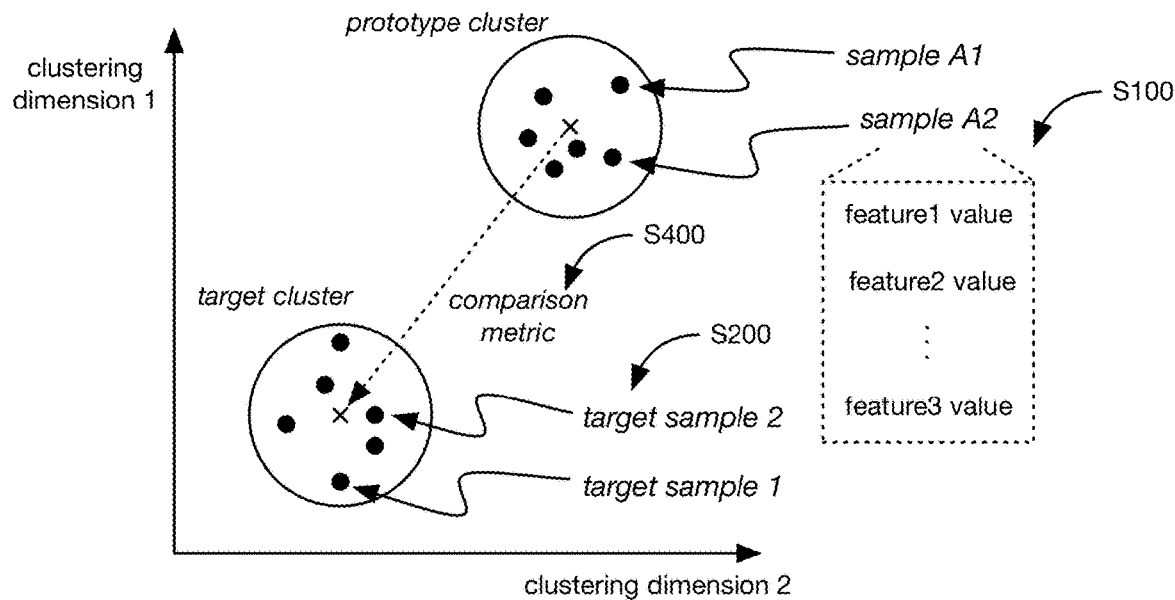
FIG. 9A depicts a second illustrative example of a comparison metric.
Figure 9B:
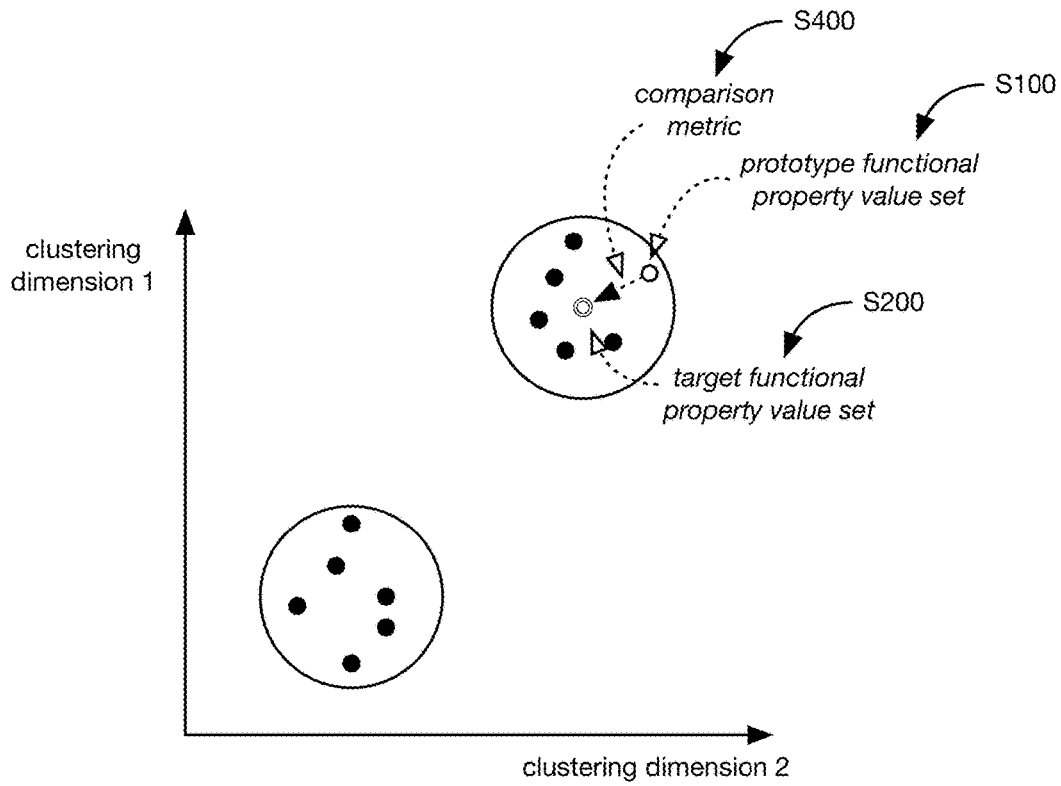
FIG. 9B depicts a third illustrative example of a comparison metric.

In this variant, the comparison metric is preferably based on a distance, but can additionally or alternatively be based on a statistical measure (e.g., correlation coefficient, outlier metric, etc.), a cosine similarity, a classification, and/or be otherwise determined. In a first example, the comparison metric can be a binary value indicating whether the prototype functional property value set is classified with a target cluster (e.g., the cluster identifier for the prototype functional property value set is the target cluster identifier associated with target functional property feature value set(s)). In a second example, the comparison metric can be a distance between the prototype functional property feature value set (plotted in N-dimensional clustering feature space) and a location associated with a target cluster (e.g., the centroid, cluster boundary, etc.); an example is shown in FIG. 8. In a third example, the comparison metric can be a distance between a location associated with a prototype cluster (e.g., the cluster associated with prototype functional property feature value set(s)) and a location associated with a target cluster; an example is shown in FIG. 9A. In a third example, the comparison metric can be a distance between the prototype functional property feature value set and the target functional property feature value set (e.g., within the same cluster, across clusters, etc.); an example is shown in FIG. 9B.

In a second variant, the comparison metric can be determined (e.g., predicted, inferred, etc.) using an algorithm applied to the prototype functional property feature values and target functional property feature values. In a first example, the algorithm can include a difference, a ratio, and/or any other comparison algorithm for each functional property feature and/or for aggregated functional property features. In a first specific example, the comparison metric is a vector of differences (e.g., differences, squared differences, etc.) between values for each functional property feature. In a second specific example, the comparison metric is a subset of functional property features with a difference (e.g., significant difference, difference above a threshold, the greatest differences, etc.) between the prototype functional property feature value and the target functional property feature value. In a second example, the algorithm can include a vector distance calculation between a vectorized prototype functional property feature value set and a vectorized target functional property feature value set.

In a third variant, the comparison metric can be a classification (e.g., determined using the characterization model). In a first example, the comparison metric can classify similarity (e.g., in discrete bins). In a second example, the comparison metric can classify a prototype as one of a set of sample classes (e.g., based on the distance between the prototype and each sample in feature space), wherein one or more of the sample classes is a target class. In an illustrative example, the comparison metric is a binary value indicating whether the prototype was classified in the target class.

In any variant, the target can be a positive target, be a negative target, and/or include both positive and negative targets. In a first example, the comparison metric can be calculated based on whether the cluster location for the prototype functional property feature value set is closer to a positive or negative target cluster. In a second example, the comparison metric can increase when the prototype functional property feature values are more similar to positive targets and decrease when the prototype functional property feature values are more similar to negative targets (or vice versa). In a third example, the comparison metric can be calculated based on whether the prototype functional property feature value set is classified as a positive or negative target class.

However, prototype functional property values and target functional property values can be otherwise compared.

Determining variable values for a prototype S500 can function to determine how to adjust variable values for a subsequent prototyping iteration, to determine variable values that will produce a prototype matching a target, and/or to select a prototype that most closely mimics a target. S500 can be performed after S200, after S400, without S400, after S600 (e.g., using a trained variable value model), after S650, and/or at any other time. S500 can optionally be iteratively performed (e.g., iteratively updating variable values for a successive prototype). After the variable values have been determined for the prototype (e.g., the second prototype), all or parts of the method can be optionally repeated for this prototype (e.g., wherein S100 is performed for the second prototype and S500 is repeated to determine variable values for a third prototype).

The variable values can be determined using one or more models (e.g., the variable value model, characterization model, etc.), rules, heuristics, equations, selection methods, optimization methods (e.g., Bayesian optimization methods including single-objective Bayesian optimization, multi-objective Bayesian optimization, Bayesian optimal experimental design, etc.), with user input (e.g., manually determined, determined using domain knowledge, modifying a model prediction, etc.), randomly determined, and/or otherwise determined.

Figure 3A:
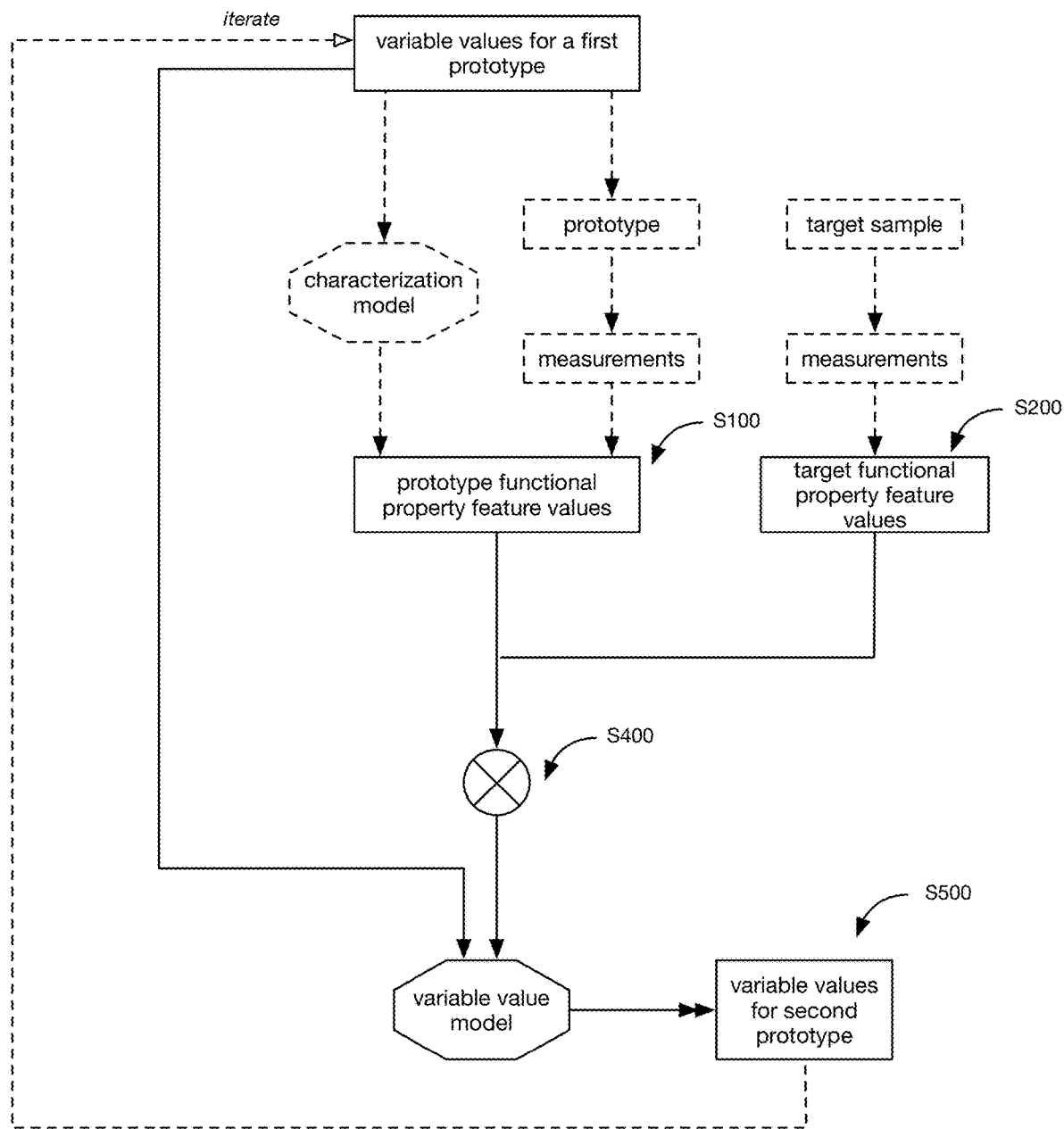
FIGS. 3A-3D depict examples of determining variable values.
Figure 3B:
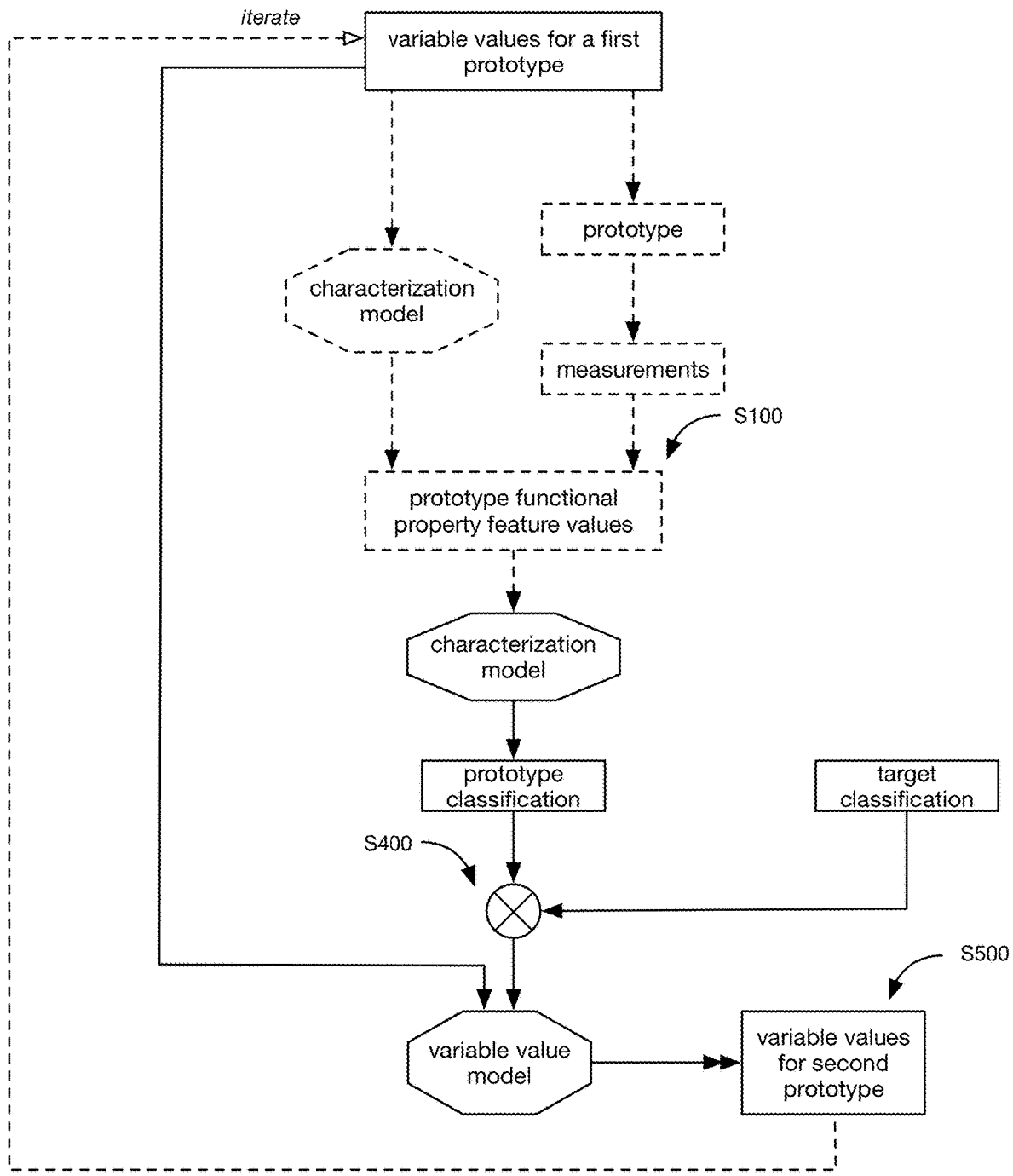
Figure 3C:
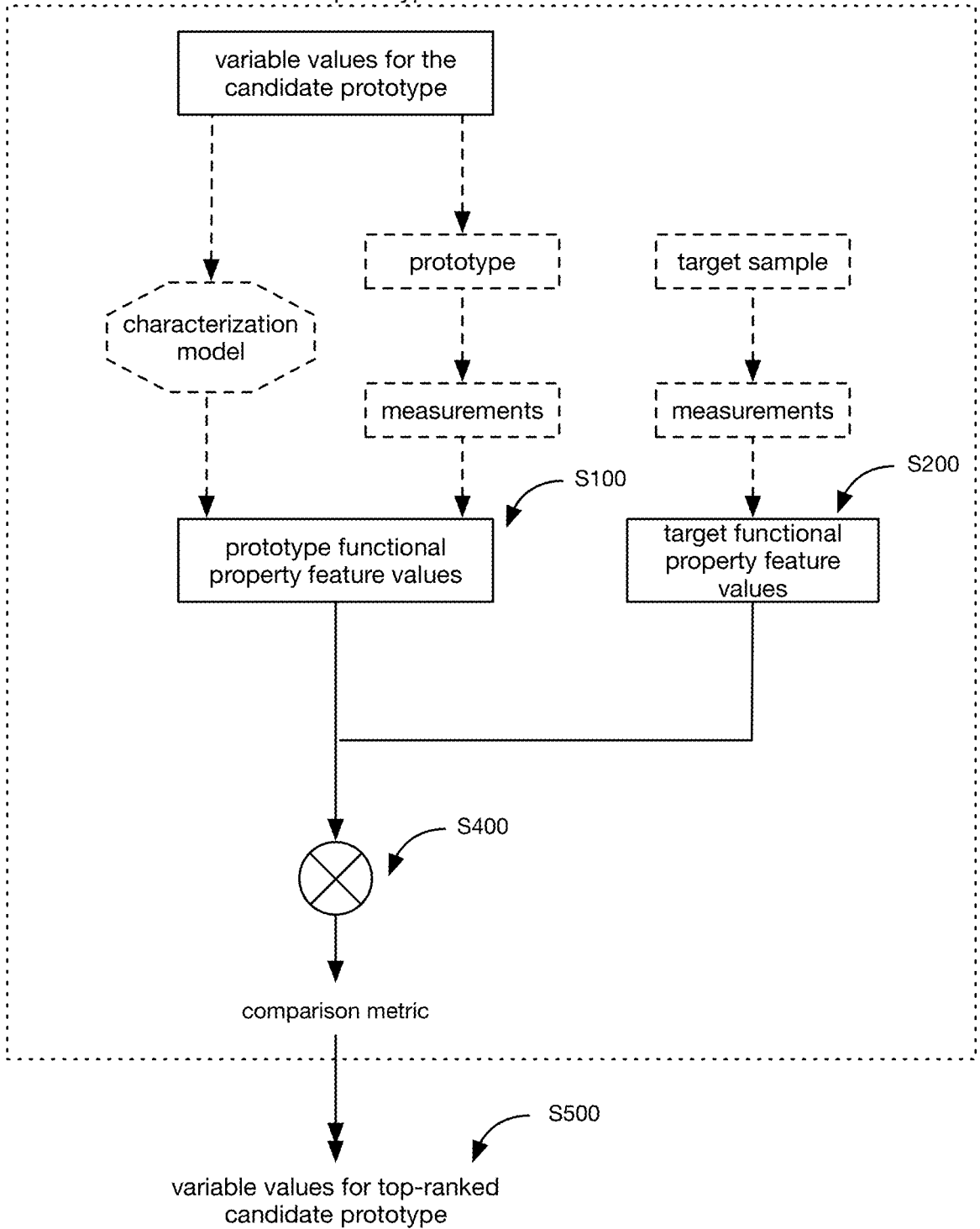

In a first variant, S500 includes selecting a prototype (with associated variable values) from a set of candidate prototypes based on characterization values determined for each candidate prototype. In an example, the candidate prototypes—each with different variable values—can be ranked based on their associated characterization values (e.g., a comparison metric determined via S400, functional property feature values determined via S100, etc.), wherein the top-ranked prototype is selected (e.g., using the variable value model, using a heuristic, etc.). The top-ranked prototype can be: the prototype that is the closest overall to a positive target, the overall furthest from a negative target, the prototype with a specific feature value closest and/or furthest from a target, and/or be otherwise defined. An example is shown in FIG. 3C.

In a second variant, the variable values can be updated variable values for a second prototype, determined based on the sample characterization values (e.g., comparison metric) and variable values for a first prototype. Examples are shown in FIG. 3A and FIG. 3B.

In a first embodiment of the second variant, S500 can include predicting (e.g., using the characterization model) an impact of an increase and/or decrease of a variable value (relative to the first prototype variable values) on the sample characterization values, wherein a variable value resulting in a desired sample characterization value change can be selected for the second prototype. In examples, the desired sample characterization value change can be an increase or decrease in the comparison metric, a change in one or more functional property feature values, a change in a sample classification, and/or any other change.

In a second embodiment of the second variant, S500 can include determining variable values based on a functional property feature value gap between the first prototype functional property feature values and the target functional property feature values (e.g., wherein the gap is the comparison metric determined via S400). The gap can include a positive and/or negative difference for each functional property feature, a vector distance from prototype functional property feature values to target functional property feature values, and/or any other comparison metric. In a first example, the variable values for the second prototype) can then be predicted (e.g., using the variable value model) based on the variable values for the first prototype and the functional property feature value gap. In a second example, one or more deviant functional property features can be identified based on the gap, wherein the values for the deviant functional property features differ (e.g., significantly differ) between the first prototype and the target. The one or more functional properties associated with the deviant functional property feature(s) can then be surfaced to a user, wherein the user selects a new variable value (e.g., based on the surfaced functional properties and domain knowledge).

In a third embodiment of the second variant, characterization values for the first prototype can be determined using the characterization model, wherein explainability and/or interpretability methods can be applied to the characterization model to determine the updated variable values. In a first illustrative example, the characterization model outputs a (predicted) non-target classification for the first prototype based on the first prototype variable values, and explainability methods are used to identify the variable values that can be adjusted (and how the variable values can be adjusted) to increase the likelihood that the characterization model will output a (predicted) target classification for the second prototype. In a second illustrative example, the characterization model outputs a (predicted) non-target classification for the first prototype based on the first prototype functional property feature values, and explainability methods are used to identify the functional property feature values that are highly influential in causing the non-target classification. The updated variable values can then be determined based on the identified functional property feature values (e.g., using variable value model; manually updating variable values based on the functional property associated with the identified functional property feature values; etc.).

In a fourth embodiment of the second variant, the sample characterization values (e.g., comparison metric) and variable values for a first prototype can be used to train a first model, and the updated variable values can be determined using a second model. For example, Bayesian optimization methods can be used to select updated variable values (e.g., to optimize variable value exploration, to optimize the sample characterization of the next prototype iteration, etc.). In a specific example, the first model can be a surrogate model (e.g., approximating an objective function), wherein inputs to the surrogate model can include variable values, and outputs from the surrogate model can include a sample characterization. In a specific example, the second model can be an acquisition function, wherein inputs to the acquisition function can include the (trained) first model, and outputs from the acquisition function can include variable values. In an illustrative example, the updated variable values can be the next query point identified via a Bayesian optimization method using the first model as a Bayesian optimization surrogate model and the second model as the Bayesian optimization acquisition function.

Figure 3D:
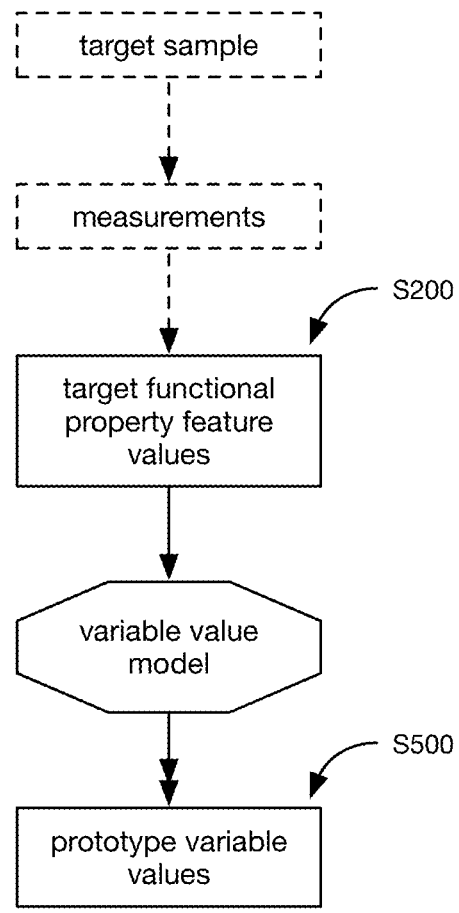

In a third variant, the variable values can be (directly) predicted based on target sample characterization values (e.g., target functional property feature values). An example is shown in FIG. 3D. In an example, the variable values can be predicted such that a prototype manufactured based on the predicted variable values will likely result in the target functional property feature values. The variable values are preferably predicted using the variable value model, but can additionally or alternatively be predicted using the characterization model, the correlation model (e.g., with a mapping between variable values and functional property feature values determined using the correlation model), any other model, domain knowledge, and/or otherwise predicted.

However, variable values for a prototype can be otherwise determined.

Optionally, the method can include training a variable value model S600, which functions to train the variable value model to predict variable values. S600 can be performed before S500, after S650, concurrently with S650, asynchronously from S650, after a set of samples have been characterized with sample characterization values (e.g., using S100/S200 methods, using S400 methods, etc.), iteratively, periodically (e.g., a new samples are characterized), and/or at any other time.

Training the variable value model can include determining training data for a set of training samples (e.g., characterized samples), wherein the training data can include: variable values, sample characterization values (e.g., functional property feature values, classifications, comparison metrics, etc.), and/or any other data for each of the set training samples. The training data can be predetermined (e.g., predetermined target characterization values), measured and/or determined based on measurements (e.g., using S100/S200 methods), synthetically generated, randomly determined, and/or otherwise determined.

Figure 5A:
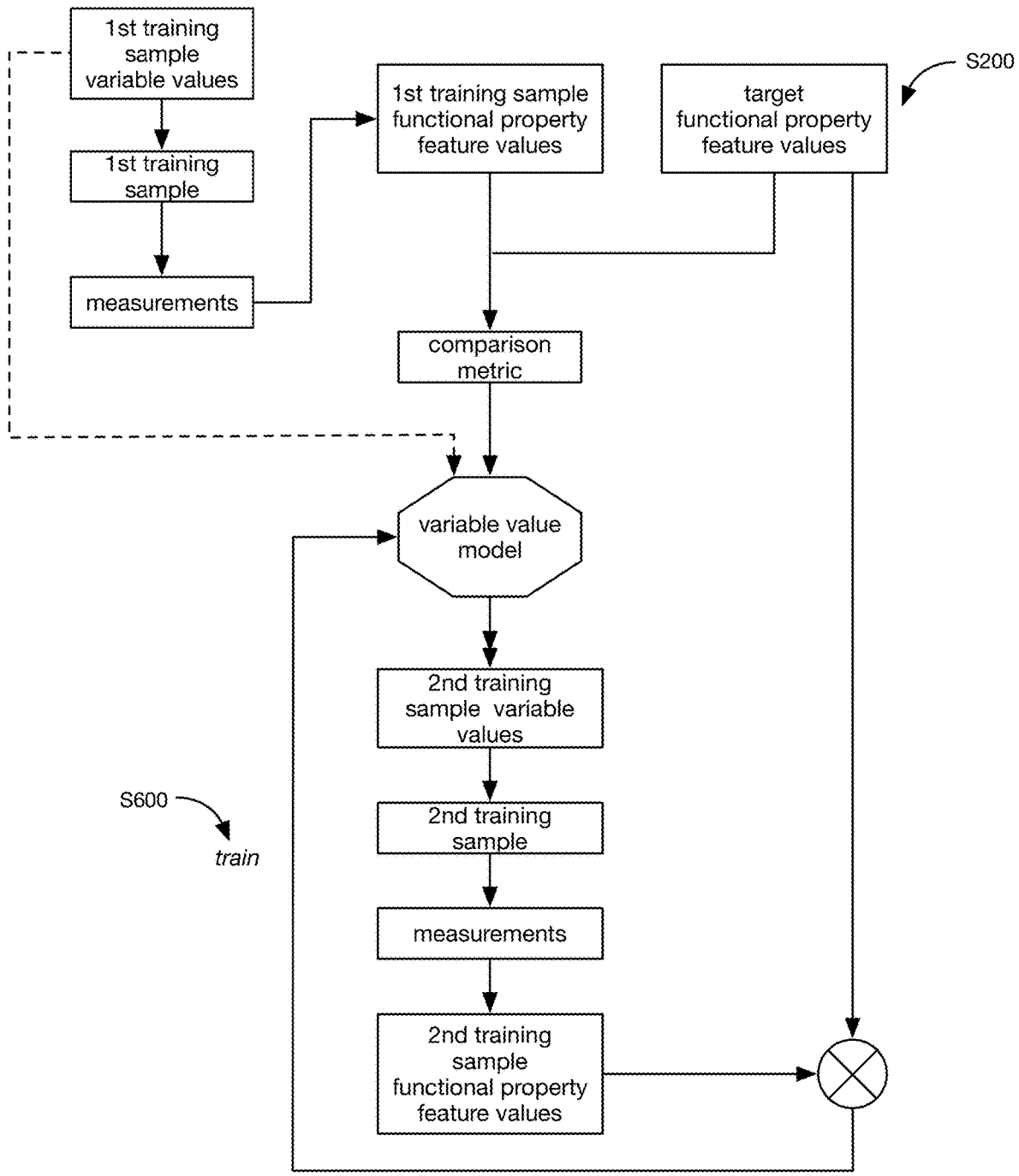
FIG. 5A depicts a first example of training a variable value model (e.g., a variable value model depicted in FIG. 3A).
Figure 5B:
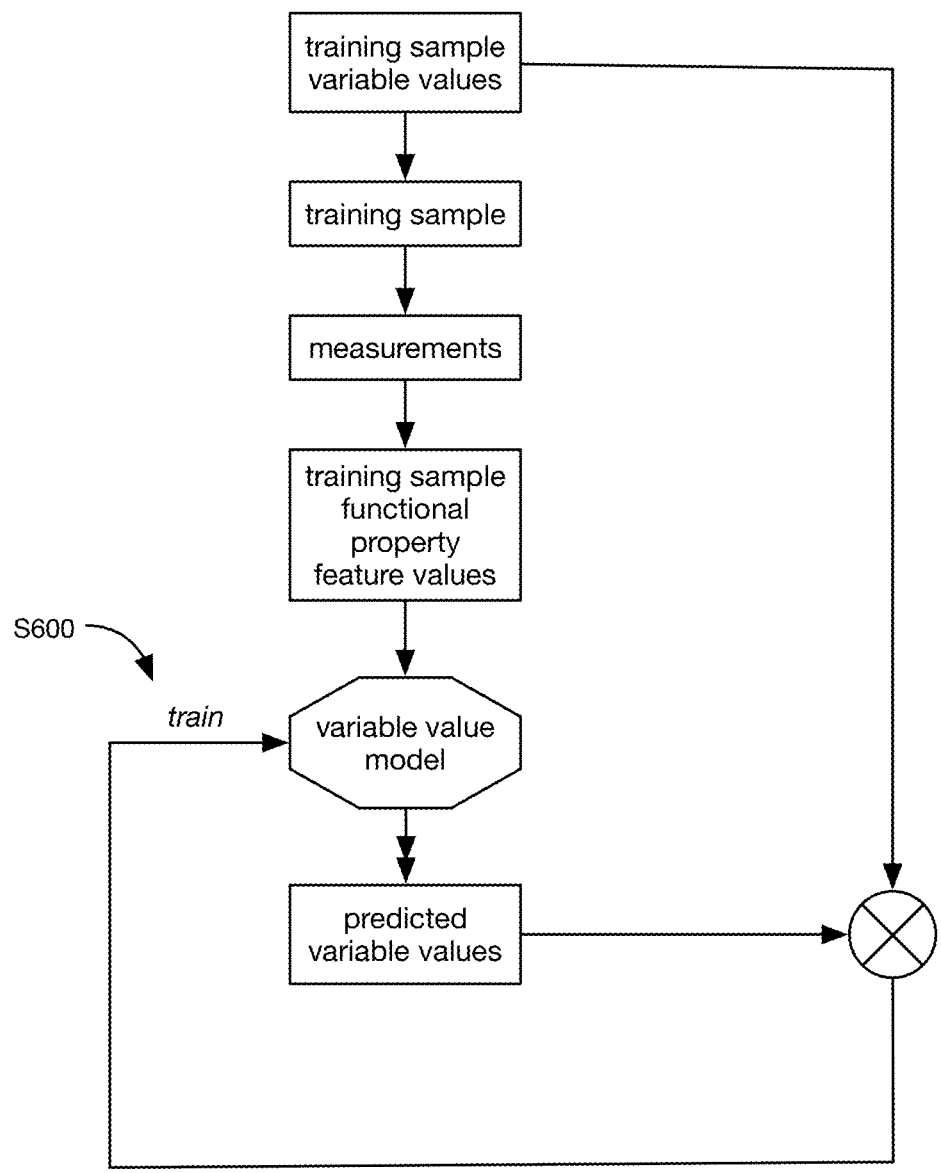
FIG. 5B depicts a second example of training a variable value model (e.g., a variable value model depicted in FIG. 3D).
Figure 5C:
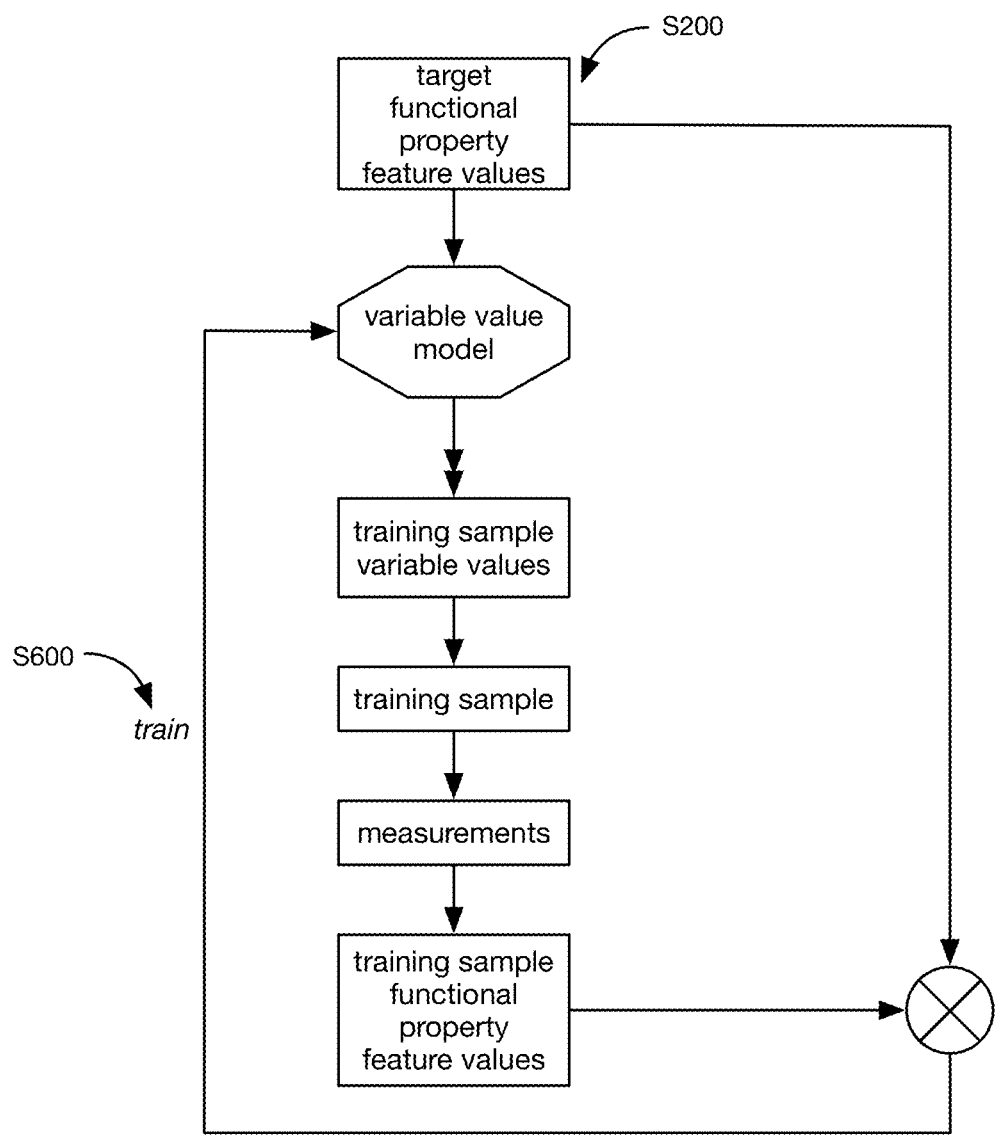
FIG. 5C depicts a third example of training a variable value model (e.g., a variable value model depicted in FIG. 3D).

In a first embodiment, the variable value model can be trained to output variable values for a prototype based on input sample characterization values (e.g., target functional property feature values). In a first example, the variable value model can be trained based on feedback from a comparison between predicted variable values (e.g., predicted based on actual sample characterization values for a training sample using the variable value model) and the actual variable values for the training sample. An example is shown in FIG. 5B. In a second example, the variable value model can be trained based on feedback from a comparison between target characterization values and characterization values (e.g., functional property feature values) determined based on measurements for a training sample manufactured using variable values predicted using the variable value model (e.g., predicted based on the target characterization values). An example is shown in FIG. 5C. In a third example, the variable value model (e.g., an encoder) can be trained to encode sample characterization values (e.g., functional property feature values) and variable values into the same latent space, wherein variable values are predicted by decoding input sample characterization values (e.g., target functional property feature values) into target variable values. For example, the variable model can be trained to encode the sample characterization values for a training sample and the corresponding variable values for the same training sample to the same point in latent space.

In a second embodiment, the variable value model is trained to output variable values for a second prototype based on variable values for a first prototype and the comparison metric for the first prototype relative to a target (e.g., where the second prototype variable values are calculated to improve the comparison metric relative to the same target). The variable values can be output as a specific value and/or a desired change (e.g., based on an output from the correlation model). For example, the variable value model can be trained based on feedback from a comparison between target characterization values and characterization values determined based on measurements for a second training sample manufactured using predicted variable values (e.g., predicted based on the comparison metric for a first training sample using the variable value model). An example is shown in FIG. 5A.

However, the variable value model can be otherwise trained.

Optionally, the method can include training a characterization model S650, which functions to train the characterization model to predict sample characterization values (e.g., given a set of variable values). S650 can be performed before S400, before S500, before S600, concurrently with S600, asynchronously from S600, after a set of samples have been characterized with sample characterization values (e.g., using S100/S200 methods, using S400 methods, etc.), iteratively, periodically (e.g., a new samples are characterized), and/or at any other time.

Training the characterization model can include determining training data for a set of training samples (e.g., characterized samples), wherein the training data can include: variable values, sample characterization values (e.g., functional property feature values, classifications, etc.), and/or any other data for each of the set training samples. The training data can be predetermined (e.g., predetermined variable values, predetermined sample class, etc.), measured and/or determined based on measurements (e.g., using S100/S200 methods), synthetically generated, randomly determined, and/or otherwise determined.

In a first variant, the characterization model is trained to predict a characterization value (e.g., a classification) for a sample based on functional property feature values for the sample. In a first embodiment, the training data can include functional property feature values (e.g., training functional property feature values) labeled with associated sample characterization values (e.g., each set of functional property feature values corresponding to a sample is labeled with a classification for the sample). The characterization model (e.g., a classifier) can be trained based on feedback from a comparison between predicted sample characterization values (e.g., a classification predicted based on the functional property feature values for a training sample using the characterization model) and actual sample characterization values for the training sample (e.g., predetermined classification); example shown in FIG. 4B. In a specific example, training the characterization model includes clustering the training functional property feature values (e.g., sets of functional property feature values) into a set of clusters (e.g., based on the associated label), and training the characterization model to select (e.g., predict) a cluster from the set of clusters based on functional property feature values for a sample. In a second embodiment, the training data can include unlabeled functional property feature values for the training samples. For example, training the characterization model can include learning clusters for the training data (e.g., wherein the characterization model outputs a cluster identifier and/or a cluster location based on a set of functional property feature values).

Figure 4A:
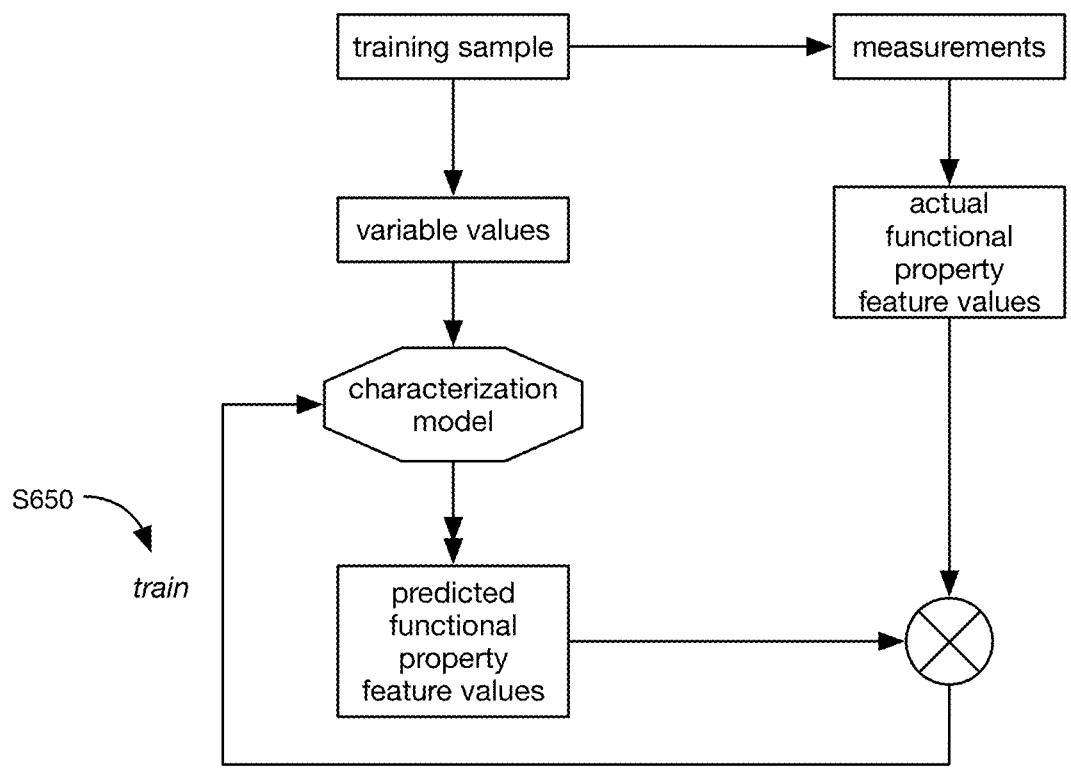
FIG. 4A depicts a first example of training a characterization model (e.g., a characterization model depicted in FIG. 3A and/or FIG. 3B).
Figure 4B:
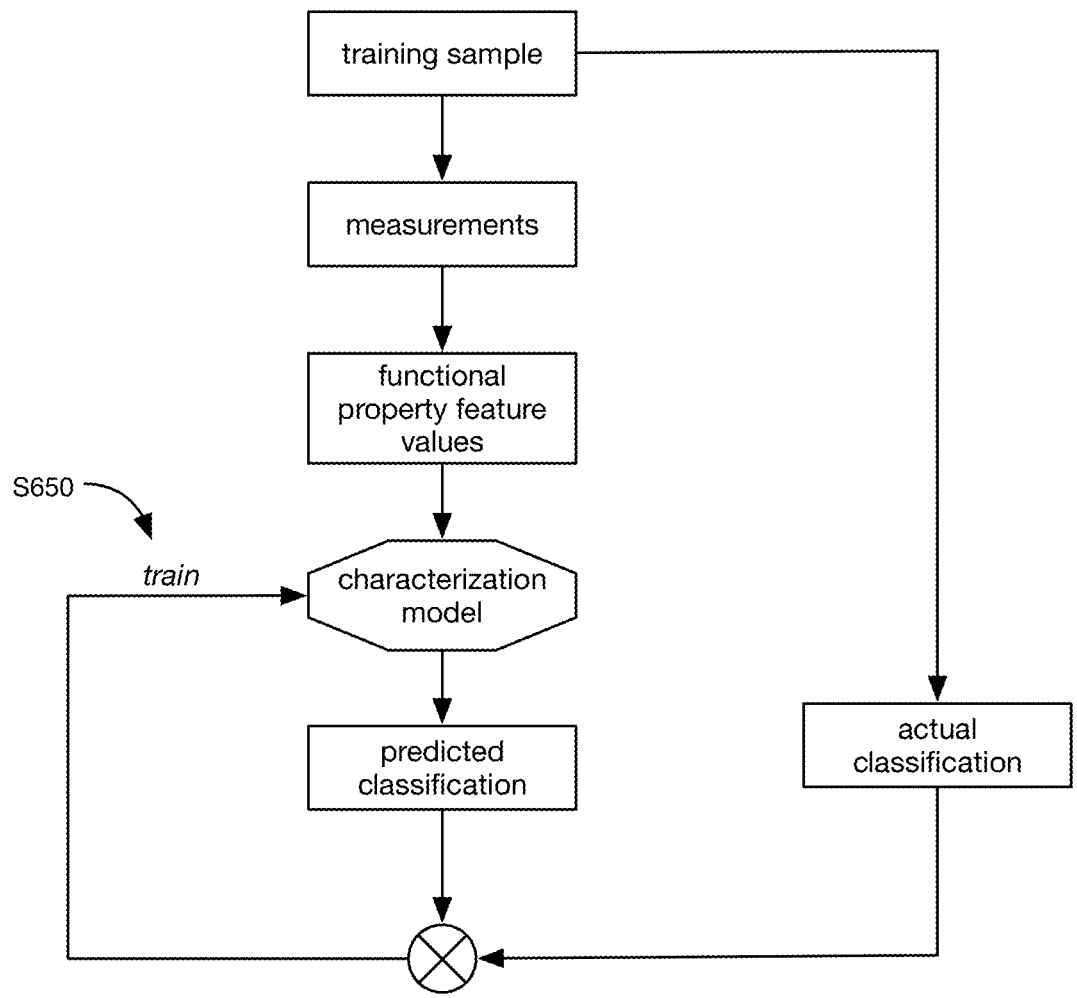
FIG. 4B depicts a second example of training a characterization model (e.g., a characterization model depicted in FIG. 3B).

In a second variant, the characterization model is trained to predict a characterization value (e.g., functional property feature values, a classification, etc.) for a sample based on variable values for the sample. For example, the training data can include variable values labeled with associated sample characterization values (e.g., measured from a sample prepared using the associated variable values, extracted from measurements, a predetermined classification, etc.). The characterization model can be trained based on feedback from a comparison between predicted sample characterization values (e.g., functional property feature values and/or other sample characterization values predicted based on the variable values using the characterization model) and actual sample characterization values. An example is shown in FIG. 4A.

In any variant, the characterization model can optionally be trained using adversarial machine learning methods. The characterization model can be trained using adversarial training data for a set of adversarial training samples. The adversarial training data can be generated (e.g., synthetically generated data, measured from physically manufactured samples, etc.) such that the characterization model (prior to training using the adversarial training data) mischaracterizes the adversarial training samples.

However, the characterization model can be otherwise trained.

The method can optionally include determining interpretability and/or explainability of a trained model (e.g., characterization model, variable value model, etc.), which can be used to identify errors in the data, identify ways of improving a model, reduce feature space, increase computational efficiency, determine influential features (e.g., a functional property feature subset) and/or values thereof, determine influential variables and/or values thereof, and/or otherwise used. Interpretability and/or explainability methods can include: local interpretable model-agnostic explanations (LIME), Shapley Additive explanations (SHAP), Ancors, DeepLift, Layer-Wise Relevance Propagation, contrastive explanations method (CEM), counterfactual explanation, Protodash, Permutation importance (PIMP), L2X, partial dependence plots (PDPs), individual conditional expectation (ICE) plots, accumulated local effect (ALE) plots, Local Interpretable Visual Explanations (LIVE), breakDown, ProfWeight, Supersparse Linear Integer Models (SLIM), generalized additive models with pairwise interactions (GA2Ms), Boolean Rule Column Generation, Generalized Linear Rule Models, Teaching Explanations for Decisions (TED), and/or any other suitable method and/or approach.

As used herein, "substantially" or other words of approximation can be within a predetermined error threshold or tolerance of a metric, component, or other reference, and/or be otherwise interpreted.

Alternative embodiments implement the above methods and/or processing modules in non-transitory computer-readable media, storing computer-readable instructions that, when executed by a processing system, cause the processing system to perform the method(s) discussed herein. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

We claim:

1. A method, comprising:
   measuring a prototype functional property signal for a prototype sample, wherein the prototype sample is associated with a set of initial manufacturing variable values;
   extracting prototype functional property feature values from the prototype functional property signal, wherein the prototype functional property feature values comprise a first prototype functional property feature value and a second prototype functional property feature value; and
   using a model, determining a set of manufacturing variable values based on a comparison between the prototype functional property feature values and target functional property feature values, wherein the comparison between the prototype functional property feature values and the target functional property feature values is determined by:
      determining a prototype characterization comprising a weighted aggregation of the first prototype functional property feature value and the second prototype functional property feature value;
      determining a target characterization based on the target functional property feature values; and
      determining a distance between the prototype characterization and the target characterization.

2. The method of claim 1, wherein the first prototype functional property feature value is determined using a first segment of the prototype functional property signal, wherein the second prototype functional property feature value is determined using a second segment of the prototype functional property signal.

3. The method of claim 1, wherein determining the target characterization based on the target functional property feature values comprises determining a target cluster based on a set of functional property feature values comprising the target functional property feature values, wherein the target characterization comprises a location associated with the target cluster.

4. The method of claim 1, wherein the prototype functional property feature values are determined using at least one of: a first derivative of at least a portion of the prototype functional property signal, a second derivative of at least a portion of the prototype functional property signal, or a peak of at least a portion of the prototype functional property signal.

5. The method of claim 1, further comprising:
   measuring a target functional property signal for a target sample; and
   extracting the target functional property feature values from the target functional property signal.

6. The method of claim 1, wherein determining the set of manufacturing variable values comprises using Bayesian optimization to select the set of manufacturing variable values.

7. The method of claim 1, wherein the set of manufacturing variable values are used to produce a food product.

8. The method of claim 1, wherein the prototype functional property signal comprises a texture measurement.

9. A method, comprising:
   producing a prototype sample using a set of manufacturing variable values; and
   evaluating the prototype sample, wherein evaluating the prototype sample comprises:
      measuring a prototype functional property signal for the prototype sample;

extracting prototype functional property feature values from the prototype functional property signal;

determining a prototype sample evaluation based on a comparison between the prototype functional property feature values and target functional property feature values; and determining an updated set of manufacturing variable values, wherein determining the updated set of manufacturing variable values comprises:
 training a first model based on the prototype sample evaluation; and
 determining the updated set of manufacturing variable values using a second model and the first model.

10. The method of claim 9, further comprising:
measuring a target functional property signal for a target sample; and
extracting the target functional property feature values from the target functional property signal.

11. The method of claim 9, further comprising normalizing the prototype functional property signal based on a peak of the prototype functional property signal, wherein the prototype functional property feature values are extracted from the normalized prototype functional property signal.

12. The method of claim 9, wherein the prototype sample comprises a plant-based dairy analog.

13. A method, comprising:
producing a prototype sample using a set of manufacturing variable values; and
evaluating the prototype sample, wherein evaluating the prototype sample comprises:
 measuring a prototype functional property signal for the prototype sample;
 extracting prototype functional property feature values from the prototype functional property signal, wherein the prototype functional property feature values comprise:
  a first prototype functional property feature value determined based on a first derivative of a first segment of the prototype functional property signal; and
  a second prototype functional property feature value determined based on a second derivative of a second segment of the prototype functional property signal; and
 determining a prototype sample evaluation based on a comparison between the prototype functional property feature values and target functional property feature values.

14. The method of claim 13, wherein the first segment is associated with a compressive force on the prototype sample, wherein the second segment is associated with tensile force on the prototype sample.

15. The method of claim 13, wherein the first prototype functional property feature value is determined based on a statistical measure of the first derivative of the first segment, and wherein the second prototype functional property feature value is determined based on a statistical measure of the second derivative of the second segment.

16. The method of claim 13, wherein the prototype functional property feature values are associated with at least one of gooeyness of the prototype sample or softness of the prototype sample.

* * * * *